United States Patent
Abudawoud et al.

(10) Patent No.: US 11,091,413 B2
(45) Date of Patent: Aug. 17, 2021

(54) METHODS OF HEAVY REFORMATE CONVERSION INTO AROMATIC COMPOUNDS

(71) Applicants: Saudi Arabian Oil Company, Dhahran (SA); Universitat Politecnica De Valencia, Valencia (ES); Consejo Superior De Investigaciones Cientificas, Madrid (ES)

(72) Inventors: Raed Hasan Abudawoud, Al-Khobar (SA); Avelino Corma Canos, Valencia (ES); M. Teresa Portilla Ovejero, Valencia (ES); Vicente J. Margarit Benavent, Valencia (ES); M. Teresa Navarro Villalba, Valencia (ES); M. Cristina Martinez Sanchez, Valencia (ES); Ibrahim M. Al-Zahrani, Dammam (SA)

(73) Assignees: Saudi Arabian Oil Company, Dhahran (SA); Universitat Politecnica De Valencia, Valencia (ES); Consejo Superior De Investigaciones Cientificas, Madrid (ES)

(*) Notice: Subject to any disclaimer, the term of this patent is extended or adjusted under 35 U.S.C. 154(b) by 0 days.

(21) Appl. No.: 16/299,723

(22) Filed: Mar. 12, 2019

(65) Prior Publication Data
US 2019/0284114 A1    Sep. 19, 2019

(30) Foreign Application Priority Data
Mar. 14, 2018    (EP) .................................... 18382168

(51) Int. Cl.
*C07C 6/12* (2006.01)
*B01J 29/26* (2006.01)
(Continued)

(52) U.S. Cl.
CPC ............... *C07C 6/126* (2013.01); *B01J 29/22* (2013.01); *B01J 29/24* (2013.01); *B01J 29/26* (2013.01);
(Continued)

(58) Field of Classification Search
None
See application file for complete search history.

(56) References Cited

U.S. PATENT DOCUMENTS

| 4,467,129 A | 8/1984 | Iwayama et al. |
| 4,963,337 A | 10/1990 | Zones |

(Continued)

FOREIGN PATENT DOCUMENTS

| CN | 101121132 A | 2/2008 |
| CN | 101121137 A | 2/2008 |

(Continued)

OTHER PUBLICATIONS

Liu et al. "Catalytic Properties of Hierarchical Mordenite Nanosheets Synthesized by Self-Assembly Between Subnanocrystals and Organic Templates" Catalytic Letters (2016) 146:249-254, S1-S7 (Year: 2016).*

(Continued)

*Primary Examiner* — Philip Y Louie
*Assistant Examiner* — Alyssa L Cepluch
(74) *Attorney, Agent, or Firm* — Dinsmore & Shohl LLP

(57) ABSTRACT

Method of making BTX compounds including benzene, toluene, and xylene, including feeding heavy reformate to a reactor containing a composite zeolite catalyst. The composite zeolite catalyst includes a mixture of layered mordenite (MOR-L) comprising a layered or rod-type morphology with a layer thickness less than 30 nm and ZSM-5. The MOR-L, the ZSM-5, or both include one or more impregnated metals. The method further includes producing the (Continued)

BTX compounds by simultaneously performing transalkylation and dealkylation of the heavy reformate in the reactor. The composite zeolite catalyst is able to simultaneously catalyze both the transalkylation and dealkylation reactions.

8 Claims, 13 Drawing Sheets

(51) Int. Cl.
| | |
|---|---|
| B01J 29/48 | (2006.01) |
| B01J 35/10 | (2006.01) |
| C07C 4/18 | (2006.01) |
| B01J 29/80 | (2006.01) |
| B01J 35/02 | (2006.01) |
| B01J 29/46 | (2006.01) |
| B01J 35/00 | (2006.01) |
| B01J 29/24 | (2006.01) |
| B01J 29/44 | (2006.01) |
| B01J 29/22 | (2006.01) |
| B01J 29/06 | (2006.01) |
| C07C 15/04 | (2006.01) |
| C07C 15/06 | (2006.01) |
| C07C 15/08 | (2006.01) |

(52) U.S. Cl.
CPC .............. *B01J 29/44* (2013.01); *B01J 29/46* (2013.01); *B01J 29/48* (2013.01); *B01J 29/80* (2013.01); *B01J 35/002* (2013.01); *B01J 35/023* (2013.01); *B01J 35/026* (2013.01); *B01J 35/1004* (2013.01); *B01J 35/1019* (2013.01); *C07C 4/18* (2013.01); *B01J 35/1038* (2013.01); *B01J 35/1061* (2013.01); *B01J 2029/062* (2013.01); *B01J 2229/186* (2013.01); *C07C 15/04* (2013.01); *C07C 15/06* (2013.01); *C07C 15/08* (2013.01); *C07C 2529/26* (2013.01); *C07C 2529/48* (2013.01)

(56) References Cited

U.S. PATENT DOCUMENTS

| | | | |
|---|---|---|---|
| 5,043,513 | A | 8/1991 | Howley et al. |
| 5,120,425 | A | 6/1992 | Zones et al. |
| 5,865,986 | A | 2/1999 | Buchanan et al. |
| 5,942,651 | A | 8/1999 | Beech, Jr. et al. |
| 5,952,536 | A | 9/1999 | Nacamuli et al. |
| 7,393,989 | B2 | 7/2008 | Negiz et al. |
| 8,242,321 | B2 | 8/2012 | Boldingh et al. |
| 8,329,973 | B2 | 12/2012 | Inui et al. |
| 8,653,315 | B2 | 2/2014 | Ali |
| 9,242,236 | B2 | 1/2016 | Xie et al. |
| 2002/0092797 | A1 | 7/2002 | Choi et al. |
| 2005/0234279 | A1 | 10/2005 | Serra et al. |
| 2009/0023968 | A1 | 1/2009 | Wang et al. |
| 2009/0112034 | A1 | 4/2009 | Levin |
| 2009/0325785 | A1 | 12/2009 | Moscoso et al. |
| 2010/0029467 | A1 | 2/2010 | Inui et al. |
| 2011/0127193 | A1 | 6/2011 | Xie et al. |
| 2012/0027673 | A1 | 2/2012 | Larsen et al. |
| 2012/0083635 | A1* | 4/2012 | Boldingh ............... B01J 29/80 585/375 |
| 2012/0165558 | A1 | 6/2012 | Ryoo et al. |
| 2012/0258852 | A1 | 10/2012 | Martinez et al. |
| 2013/0261365 | A1 | 10/2013 | Wang et al. |
| 2013/0281750 | A1* | 10/2013 | Abudawoud ............ C07C 6/06 585/321 |
| 2018/0134637 | A1 | 5/2018 | Lai et al. |

FOREIGN PATENT DOCUMENTS

| | | |
|---|---|---|
| CN | 101190418 A | 6/2008 |
| CN | 101190864 A | 6/2008 |
| CN | 101191069 A | 6/2008 |
| CN | 101347746 A | 1/2009 |
| CN | 101348407 A | 1/2009 |
| CN | 101602639 A | 12/2009 |
| CN | 101885663 A | 11/2010 |
| CN | 101811063 B | 10/2012 |
| CN | 104437611 A | 3/2015 |
| CN | 104437613 A | 3/2015 |
| EP | 042754 A1 | 6/1981 |
| EP | 109962 A1 | 6/1984 |
| EP | 1586376 A1 | 10/2005 |
| EP | 1775277 A1 | 4/2007 |
| WO | 2004046278 A1 | 6/2004 |
| WO | 2005118515 A1 | 12/2005 |
| WO | 2010150996 A2 | 12/2010 |
| WO | 2018011122 A1 | 1/2018 |
| WO | 2018071184 A1 | 4/2018 |
| WO | 2018231340 A1 | 12/2018 |

OTHER PUBLICATIONS

Dai et al. "Hierarchical mordenite zeolite nano-rods bundles favourable to bulky molecules" Chemical Physics Letters 686 (2017) 111-115 (Year: 2017).*

Sharma et al. "Synthesis and morphological studies of nanocrystalline MOR type zeolite material" Journal of Colloid and Interface Science, 2008 325, 547-557. (Year: 2008).*

Jo et al. "Capping with Multivalent Surfactants for Zeolite Nanocrystal Synthesis" Angewandte Chemie International Edition. 2013, 52, 10014-10017 (Year: 2013).*

International Search Report and Written Opinion dated Sep. 20, 2019 pertaining to International application No. PCT/US2019/021594 filed Mar. 11, 2019.

Ali et al., "Selective production of xylenes from alkyl-aromatics and heavy reformates over dual-zeolite catalyst", Catalysis Today, vol. 243, pp. 118-127 (2015).

Al-Khattaf et al., "Catalytic transformation of methyl benzenes over zeolite catalysts", Applied Catalysis A: General 394, pp. 176-190, 2011.

Calderia et al., "Properties of hierarchical Beta zeolites prepared from protozeolitic nanounits for the catalytic cracking of high density polyethylene", Applied Catalysts A: General 531, pp. 187-196, 2017.

Choi et al., "Stable single-unit-cell nanosheets of zeolite MFI as active and long-lived catalysts", Nature, vol. 461, pp. 246-250, Sep. 10, 2009.

Corma et al., "Discovery of new paraffin isomerization catalysts based on SO4 2-/ZrO2 and Wox/ZrO2 applying combinatorial techniques", Catalysts Today 81, pp. 495-506, 2003.

Han et al., Zeolite Synthesis Using Flexible Diquarternary Alkylammonium Ions (CnH2n+1)2HN+(CH2)5N+H(CnH2n+1)2 with n=1-5 as Structure-Directing Agents, Chem Mater, vol. 17, pp. 477-486, 2005.

Jackowski et al., "Diquaternary Ammonium Compounds in Zeolite Synthesis: Cyclic and Polycyclic N-Heterocycles Connected by Methylene Chains", American Chemical Society, 131, 1092-1100 (2009).

Jo et al., "Capping with Multivalent Surfactants for Zeolite Nanocrystal Synthesis", Angew. Chem, vol. 125, pp. 10198-10201, 2013 with Supporting Information.

Kim et al., "Bulk crystal seeding on generation of mesoporoes by organosilane surfactants in zeolite synthesis", Electronic Supplementary (ESI) for Journal of Masterials Chemistry A., The Royal Society of Chemistry 2014.

Kong et al., "Fabrication of core/shell structure via overgrowth of ZSM-5 layers on mordenite cyrstals", Microporous and Mesoporous Materials, vol. 119, pp. 91-96, 2009.

Konysheva et al., "Effect of Nature of Heteroelement (Ba, Ga, Al) on Adsorption of Acid Characteristics of Hierarchical Porous Zeo-

(56) References Cited

OTHER PUBLICATIONS lites of MOR, BEA and MTW Strucural Types", Theoretical and Experimental Chemistry, vol. 53, No. 6, pp. 410-416, Jan. 2018.
Va Laak et al., "Mesoporous mordenites obtained by sequential acid and alkaline treatments—Catalysts for cumene production with enhanced accessibility", Journal of Catalysis, vol. 276, pp. 170-180, 2010.
Lee et al., "Reinvestigation into the synthesis of zeolites using diquaternary alkylammonium ions (CH3)3N+(CH2)nN+(CH3)3 with n=3-10 as structure-directing agents", Microporous and Mesoporous Materials, vol. 68, pp. 97-104, 2004.
Lee et al., "Zeolite synthesis in the presence of flexible diquaternary alkylammonium ions (C2H5)3N+(CH2)nN+(C2H5)3 with n+3-10 as structure-directing agents", Microporous and Mesoporous Materials, vol. 60, pp. 237-249, 2003.
Li et al., "One-pot synthesis of hierarchical mordenite and its performance in the benzylation of benzene with benzyl alcohol", J. Matter Sci, vol. 50, pp. 5059-5067, 2015.
Mihayli et al., "Transformation of ethylbenzene-m-xylene misture on zeolites with different structures", J. Porous Matter, vol. 21, pp. 485-493, 2014.
Liu et al., "Catalytic Properties of Hierarchical Mordenite Nanosheets Synthesized by Self-Assembly Between Subnanocrystals and Organic Templates", Catal Lett, vol. 146, pp. 249-254, 2016 with Electronic Supplementary Information.
Moller et al., "Mesoporosity—a new dimension for Zeolites", Chem Soc Rev. vol. 42, pp. 3689-3707, 2013.
Ordomsky et al., "Cumene disproportionation over micro/mesoprous catalysts obtained by recrystallization of mordenite", Journal of Catalysis, vol. 295, pp. 207-216, 2012.
Shvets et al., "New Approaches to Creation of Micro- and Mesoporous Functional Materials", Theoretical and Experimental Chemiustry, vol. 53, No. 5, Nov. 2017.
Thommes et al., "Physisorption of gases, with special reference to the evaluation of surface area and pore size distribution (IUPAC Technical Report)", Pure Appl. Chem., 87(9-10), pp. 1051-1069, 2015.
Verboekend et al., "Design of hierarchical zeolite catalysts by desilication", Catalysis Science & Technology, vol. 1, pp. 879-890, 2011.
Vitvarova et al., "Catalytic applications and FTIR investigation of zeolite SSZ-33 after isomorphous substitution", Microporous and Mesoporous Materials, vol. 194, pp. 174-182, 2014.
Zones et al., "Boron-beta zeolite hydrothermal conversions: the influence of template structure and of boron concentration and source", Microporous Materials, vol. 2, pp. 543-555, 1994.
European Search Report pertaining to European Application No. 18382172.7 dated Jan. 4, 2019.
European Search Report pertaining to European Application No. 18382170.1 dated Sep. 27, 2018.
European Search Report pertaining to European Application No. 18382168.5 dated Sep. 27, 2018.
European Search Report pertaining to European Application No. 18382167.7 dated Jan. 4, 2019.
European Search Report pertaining to European Application No. 18382169.3 dated Sep. 27, 2018.
European Search Report pertaining to European Application No. 18382171.9 dated Oct. 5, 2018.
Galarneau et al., Validity of the t-plot Method to Assess Microporosity in Hierarchical Micro/Mesoporous Materials, Langmuir 2014, 9 pgs.
International Search Report and Written Opinion dated Jun. 27, 2019 pertaining to International application No. PCT/US2019/021592 filed Mar. 11, 2019, 15 pgs.
International Search Report and Written Opinion dated Jun. 28, 2019 pertaining to International application No. PCT/US2019/021597 filed Mar. 11, 2019, 17 pgs.
International Search Report and Written Opinion dated Jun. 26, 2019 pertaining to International application No. PCT/US2019/021590 filed Mar. 11, 2019, 23 pgs.
International Search Report and Written Opinion dated Jun. 26, 2019 pertaining to International application No. PCT/US2019/021595 filed Mar. 11, 2019, 20 pgs.
Office Action dated Dec. 2, 2019 pertaining to U.S. Appl. No. 16/299,717, filed Mar. 12, 2019, 26 pgs.
Office Action dated Dec. 20, 2019 pertaining to U.S. Appl. No. 16/299,838, filed Mar. 12, 2019, 30 pgs.
Office Action dated Dec. 20, 2019 pertaining to U.S. Appl. No. 16/299,844, filed Mar. 12, 2019, 31 pgs.
Machine translation CN 101811063, Aug. 25, 2010, retrieved Dec. 6, 2019 (Year: 2019).
Camblor et al. "Characterization of Nanocrystalline Zeolite Beta" Microporous and Mesoporous Materials 25 (1998) pp. 59-74 (Year: 1998).
Notice of Allowance and Fee(s) Due dated Apr. 17, 2020 pertaining to U.S. Appl. No. 16/299,832, filed Mar. 12, 2019, 31 pgs.
Notice of Allowance and Fee(s) Due dated Apr. 8, 2020 pertaining to U.S. Appl. No. 16/299,704, filed Mar. 12, 2019, 31 pgs.
Office Action dated Jun. 24, 2020 pertaining to U.S. Appl. No. 16/299,838, filed Mar. 12, 2019, 22 pgs.
Office Action dated Jun. 29, 2020 pertaining to U.S. Appl. No. 16/299,844, filed Mar. 12, 2019, 23 pgs.
Office Action dated Oct. 14, 2020 pertaining to U.S. Appl. No. 16/299,844, filed Mar. 12, 2019, 15 pgs.
Notice of Allowance and Fee(s) Due dated Oct. 14, 2020 pertaining to U.S. Appl. No. 16/299,838, filed Mar. 12, 2019, 9 pgs.

* cited by examiner

METHODS OF HEAVY REFORMATE CONVERSION INTO AROMATIC COMPOUNDS

CROSS REFERENCE TO RELATED APPLICATIONS

This application claims priority to European Application No. 18382168.5, filed Mar. 14, 2018 which is hereby incorporated by reference in its entirety.

TECHNICAL FIELD

Embodiments of the present specification generally relate to methods of making aromatic compounds, and specifically relate to methods of making benzene, toluene, and xylenes from a heavy reformate feed and a catalyst for utilization in the same.

BACKGROUND

Heavy reformate (HR), containing mainly $C_{9+}$ aromatics, is the fraction that remains after extraction of the more valuable BTX (benzene, toluene, xylene) fraction from the catalytic reformate or the pyrolysis gasoline. Traditionally this fraction was directly added to the gasoline pool. However, due to the restriction of the benzene content in gasoline by environmental regulations, it is important to find alternative ways of upgrading this stream into other valuable products. One option is to convert the heavy aromatics in the heavy reformate into additional BTX compounds. Heavy reformate may be converted into xylenes, benzene, and toluene by dealkylation of the $C_9$ alkylaromatics to produce toluene, and further transalkylation of the toluene formed by dealkylation with other $C_{9+}$ alkylaromatics present in the feed to produce benzene and xylenes. Regardless, these means to produce BTX compounds by simultaneous dealkylation and transalkylation have limited efficiency, because of the sequential nature of the conversion reaction process where products of a first reaction are utilized in a second reaction.

SUMMARY

Accordingly, ongoing needs exist for catalysts suitable for efficiently converting heavy reformates to produce benzene, toluene, and xylenes. Embodiments of the present disclosure are related to composite zeolite catalyst formulations and methods of making benzene, toluene, and xylenes using the composite zeolite catalyst. The composite zeolite catalysts may convert a mixture of heavy aromatic compounds (such as those present in heavy reformate), particularly $C_{9+}$ aromatic hydrocarbons to benzene, toluene, and xylenes, and particularly to commercially valuable xylenes.

According to one embodiment, a method of making BTX compounds including benzene, toluene, and xylene is provided. The method includes feeding heavy reformate to a reactor. The reactor contains a composite zeolite catalyst including a mixture of layered mordenite (MOR-L) having a layered or rod-type morphology with a layer thickness less than 30 nanometers (nm) and ZSM-5. The MOR-L, the ZSM-5, or both include one or more impregnated metals. The method further includes producing the BTX compounds by simultaneously performing transalkylation and dealkylation of the heavy reformate in the reactor. The composite zeolite catalyst is able to simultaneously catalyze both the transalkylation and dealkylation reactions.

According to another embodiment, a composite zeolite catalyst is provided. The composite zeolite catalyst includes a mixture of layered mordenite (MOR-L) having a layered or rod-type morphology with a layer thickness less than 30 nm and ZSM-5. The MOR-L, the ZSM-5, or both comprise one or more impregnated metals.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

DETAILED DESCRIPTION

Figure 1:
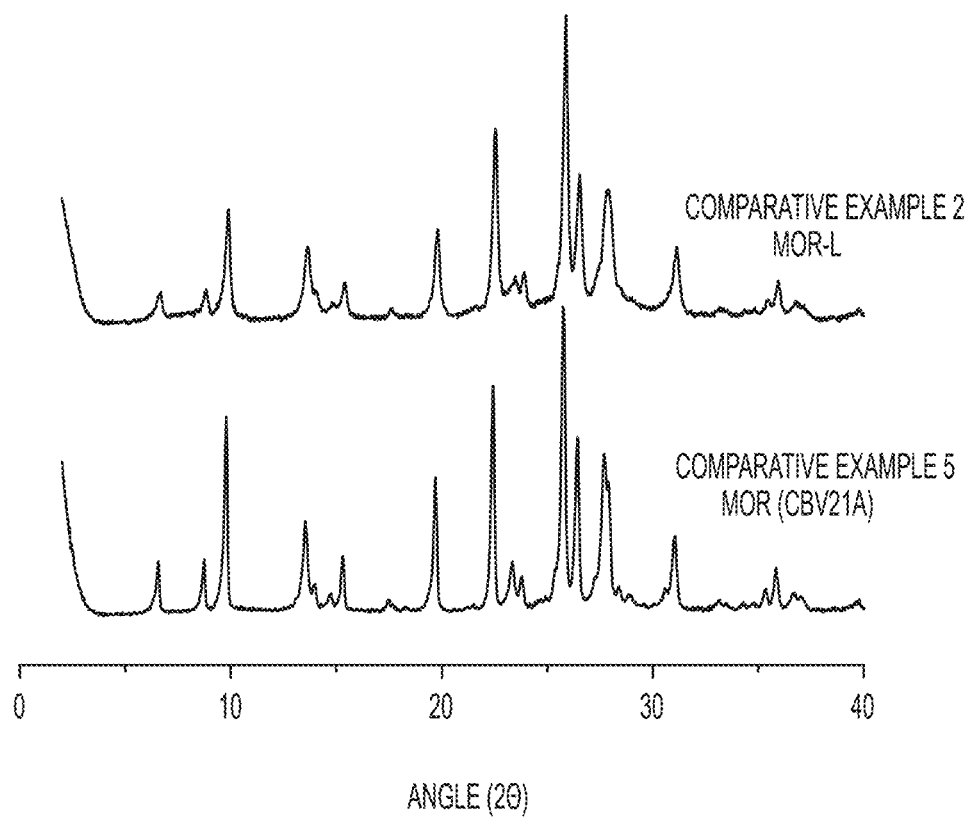
FIG. 1 is an X-Ray Diffraction (XRD) pattern of commercially available Mordenite and Layered Mordenite (MOR-L).

Reference will now be made in detail to embodiments of a method of making benzene, toluene, and xylene by conversion of heavy reformate with a composite zeolite catalyst.

The main components of heavy reformate are ethyltoluenes (methyl-ethyl-benzenes, MEB) and trimethyl-benzenes (TMB). The structures of the MEB isomers and TMB isomers are provided infra.

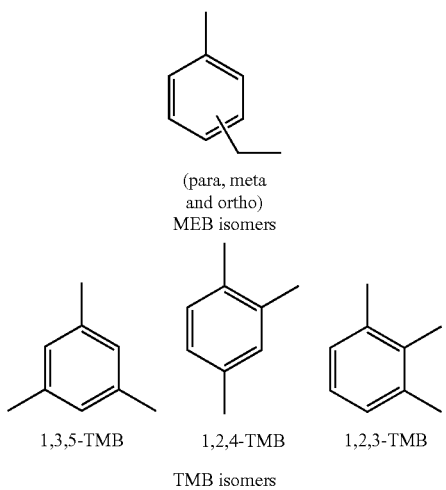

These aromatics can be converted into the more valuable BTX compounds by means of dealkylation of the $C_{9+}$ alkylaromatics, or by transalkylation of these compounds with benzene or toluene. The aim of the process is to maximize the production of xylenes by de-ethylation of MEB and transalkylation of TMB. Specifically, transalkylation of TMB present in the feed with the toluene formed as a product of de-ethylation of MEB.

The dealkylation of MEB to toluene and ethane is provided infra. Dealkylation of MEB in the presence of a Brønsted acid catalyst initially produces toluene and ethylene. However, the ethylene may be subsequently hydrogenated to ethane in the presence of an adequate hydrogenation catalyst. If the hydrogenation functionality is not effective, portions of the ethylene may not be hydrogenated to ethane and as such may be present in the product gases, or it may be converted to oligomers or other products.

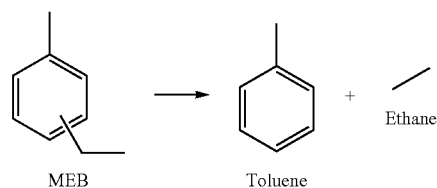

The transalkylation of TMB present in the heavy reformate with the toluene formed from dealkylation of MEB to toluene and ethane is provided infra.

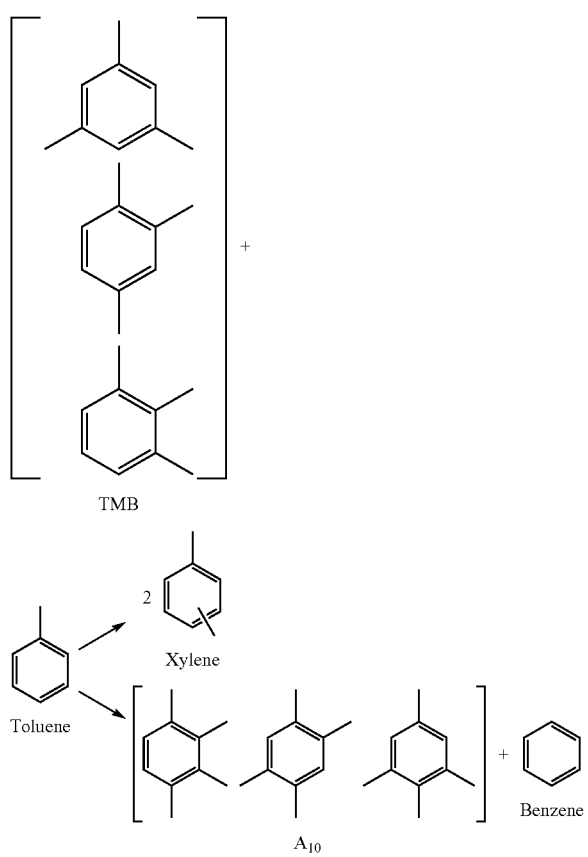

Additionally, toluene and TMB may also undergo a disproportionation reaction leading to xylenes and benzene or xylenes and tetramethylbenzenes ($A_{10}$), respectively. The chemical reactions are provided infra.

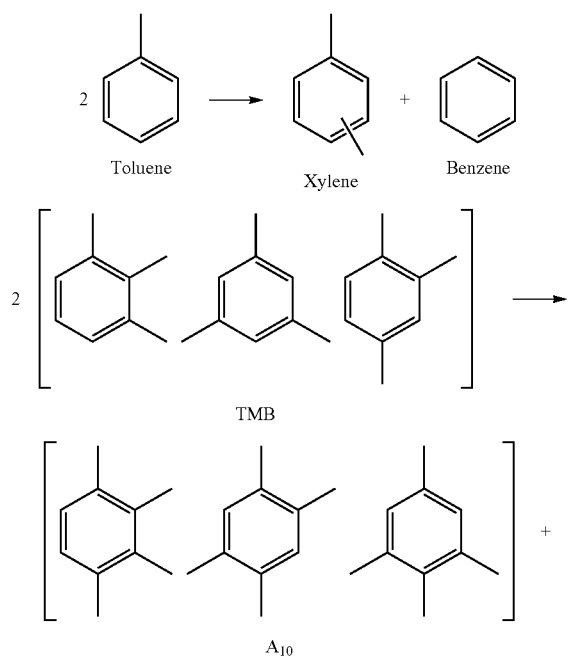

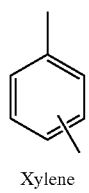

Xylene

A composite zeolite catalyst may be formed from a mixture of layered mordenite (MOR-L) and ZSM-5 zeolite catalysts. The composite zeolite catalyst allows conversion of heavy reformate, or other aromatic reactant streams, in a single reactor. Specifically, the dealkylation of MEB and the transalkylation of the produced toluene with TMB may be performed in a single reactor, because of the proximity between the crystals of MOR-L and ZSM-5 when physically mixed in a single reactor. The MEB dealkylation reaction is necessary in order to obtain the toluene that has to react with the TMB in the feed for producing the desired xylenes and benzene. Thus, the proximity of the ZSM-5 and MOR-L crystals obtained by the physical mixing of the MOR-L and ZSM-5 and reaction in a single reactor enables an improved and faster coupling of both consecutive reactions to produce benzene, toluene, and xylenes.

The composite zeolite catalyst in one or more embodiments comprises MOR-L and ZSM-5. ZSM-5 is an aluminosilicate zeolite of the pentasil family of zeolites. ZSM-5 (Zeolite Socony Mobil-5) has a Mordenite Framework Inverted (MFI) framework with an ordered crystal structure presenting intersecting 10-ring channels (5.1×5.5 and 5.3×5.6 angstrom (Å)). Mordenite (MOR), an aluminosilicate, comprises a molecular structure of a framework containing chains of five-membered rings of linked silicate and aluminate tetrahedra (four oxygen atoms arranged at the points of a triangular pyramid about a central silicon or aluminum atom), with a crystalline structure presenting mono-directional channels defined by twelve-membered rings (6.5×7.0 Å). A commercially available MOR is CBV21A from Zeolyst International (Conshohocken, Pa. USA).

Figure 2:
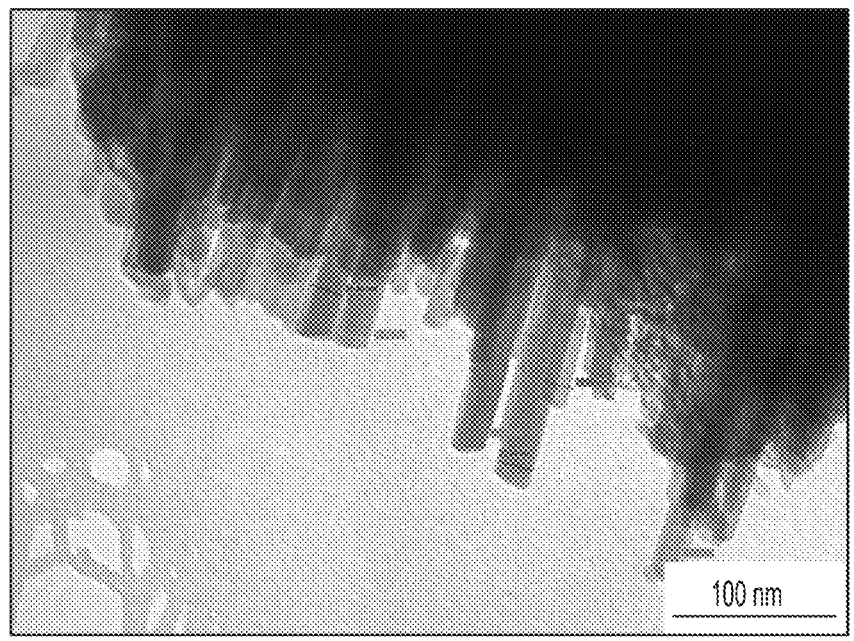
FIG. 2 is a TEM micrograph micrograph of MOR-L synthesized in accordance with one or more embodiments of the present disclosure.
Figure 3:
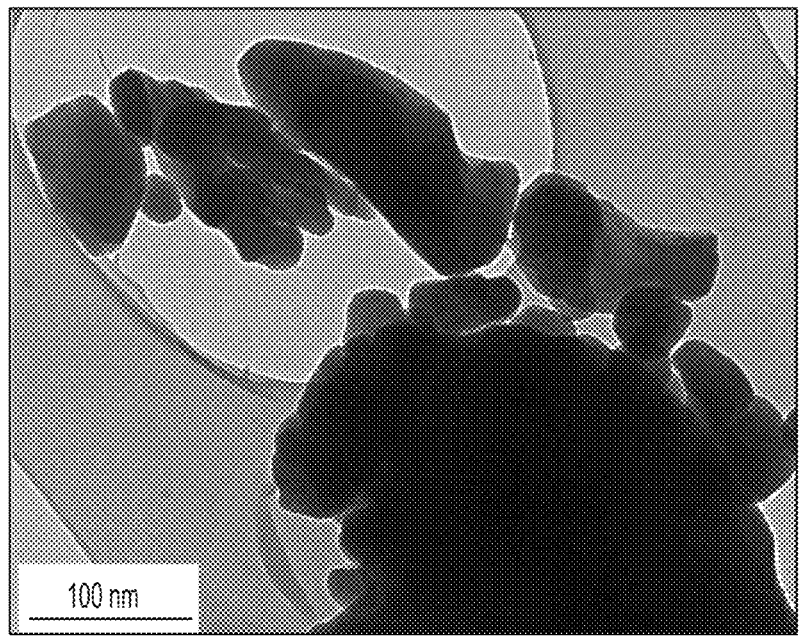
FIG. 3 is a TEM micrograph of a commercially available Mordenite (CBV21A).

Layered mordenite (MOR-L) and MOR comprise the same characteristic structure, but differing morphology. With reference to FIG. 1, the X-ray diffraction (XRD) pattern for MOR-L and MOR (CBV21A) comprise the same peaks demonstrating the same characteristic underlying the crystalline structure. With regards to the differing morphology, MOR-L comprises a layered or rod-type morphology, and MOR comprises larger crystals. FIG. 2 illustrates (TEM) images of the MOR-L crystal morphology, and clearly shows the layered shape with limited growth in one of the crystallographic directions. Similarly, FIG. 3 illustrates a TEM image of the MOR crystal morphology for the commercially available CBV21A. The crystals of MOR are heterogeneous in size and irregular in shape and larger than those of MOR-L. Additionally, the MOR crystals present no preferential growth in any of the three space directions.

The MOR-L comprises a layered or rod-type morphology. In one or more embodiments, the layer thickness of the layers or rods is less than 30 nanometers (nm). The thickness is considered the smallest dimension of the MOR-L crystal. In further embodiments, the layer thickness of the layers or rods is less than 28 nm, less than 25 nm, less than 22 nm, less than 20 nm, or less than 18 nm. The minimal layer thickness produces a MOR-L crystal with a greater external to internal surface area ratio than commercially available MOR as the MOR-L presents as sheets or long and slender rods.

The method of making BTX compounds includes feeding heavy reformate to a reactor, which contains the composite zeolite catalyst formed from a mixture of MOR-L and ZSM-5. The BTX compounds are then produced by simultaneously performing transalkylation and dealkylation of the heavy reformate in the reactor. The composite zeolite catalyst is able to simultaneously catalyze both the transalkylation and dealkylation reaction with the combination of MOR-L and ZSM-5.

The composite zeolite catalyst including both MOR-L and ZSM-5 produces a synergistic effect and is capable of converting a heavy reformate feed, generally comprising at least 15 weight percent (wt. %) MEB and at least 50 wt. % TMB, to BTX compounds within a single reactor. The presence of ZSM-5 component increases the amount of toluene in the reaction media as a result of the additional dealkylation activity originating from the ZSM-5 component. The increased availability of toluene in the reaction media allows for increased reaction with the TMB present in the heavy reformate feed in conjunction with the MOR-L to yield BTX products, especially desirable xylenes. Additionally, as the TMB has more toluene available for reaction, transalkylation of the $A_{9+}$ aromatics from the heavy reformate feed is reduced, which also reduces the generation of undesirable $A_{10+}$ by-products.

Alkylaromatics, such as those present in a heavy reformate (MEB, TMB), in the presence of an acid catalyst, may undergo undesired reactions, which lead to formation of aromatics with 10 carbon atoms ($A_{10}$) or more than 10 carbon atoms ($A_{10+}$). If these $A_{10}$ and $A_{10+}$ compounds cannot diffuse out of the zeolite crystals through the pores of the crystalline structure because of steric limitations, they may block part of the channel systems or lead to bulkier coke precursors. The improved conversion efficiency of the composite zeolite catalysts alleviates the formation of heavy alkylaromatics comprising $A_{10}$ and $A_{10+}$ aromatics. Specifically, the proximity of the ZSM-5 and MOR-L as a mixture within a single reactor allows the TMB of the feed to react preferentially with the toluene formed by dealkylation of MEB on the ZSM-5 crystals, instead of reacting with other TMB by transalkylation to form tetramethylbenzene or heavier compounds. The reaction of the heavy reformate feed in a single reaction in the presence of the composite zeolite catalyst, including ZSM-5 and MOR-L, results in higher selectivity to xylenes and reduced formation of $A_{10+}$ and coke precursors, leading therefore to improved catalyst life.

The reaction of the heavy reformate feed in a single reactor with the composite zeolite catalyst comprising ZSM-5 and MOR-L achieves improved performance in conversion of the heavy reformate to BTX compounds. This improvement is even more profound when carrying out the transalkylation of a heavy reformate in the absence of added toluene or benzene, because these two aromatics must be produced in-situ from $C_{9+}$ aromatics such as with dealkylation of MEB contained within the feed. The proximate locations of the MOR-L and ZSM-5 in the composite zeolite catalyst through a physical mixture and reaction in a single reactor allows the toluene produced from dealkylation of MEB to be more readily available for use in the transalkylation reaction of TMB or disproportionation reaction of toluene for the ultimate production of xylenes.

The MOR-L and ZSM-5 zeolite catalysts may be physically mixed in various ratios to produce a composite zeolite catalyst with varying degrees of MEB and TMB conversion. In one or more embodiments, the MOR-L and ZSM-5 are combined in a 50:50 to 90:10 weight ratio to form the composite zeolite catalyst. In various further embodiments, the MOR-L and ZSM-5 are combined in a 50:50 to 80:20 weight ratio, 50:50 to 70:30 weight ratio, 55:45 to 65:35 weight ratio, or an approximately 60:40 weight ratio to form the composite zeolite catalyst. As previously indicated, an increase in ZSM-5 in the composite zeolite catalyst results in an increase in the amount of toluene in the reaction media as a result of the additional dealkylation activity originated from the ZSM-5 component. However, it will be appreciated that an increase in ZSM-5 weight percentage (wt. %) requires a congruent reduction in MOR-L wt. %. An increase in ZSM-5 wt. % and reduction in MOR-L wt. % results in less transalkylation and an excess of toluene.

Moreover, the zeolite composite catalyst may be impregnated with metals for catalysis, for example, metals such as molybdenum, chromium, platinum, nickel, tungsten, palladium, ruthenium, gold, rhenium, rhodium, or combinations thereof. In one embodiment, the impregnated metal is rhenium (Re). The metal component may exist within the final zeolite composite catalyst as a compound, such as an active metal oxide, an active metal sulfide or active metal halide, in chemical combination with one or more of the other ingredients of the composite, or as an elemental metal. The impregnated metal component may be present in the final composite zeolite catalyst in any amount that is catalytically effective, for example from 0.01 to 20.0 wt. %, or from 2 to 5 wt. %, or from 0.1 to 1.5 wt. %, or approximately 0.3 wt. % of the composite zeolite catalyst particle.

Metals are added to the catalyst for their hydrogenation functionality. The dealkylation, transalkylation and disproportionation reactions take place on the Brønsted acid sites of the composite zeolite catalysts. However, the hydrogenation function of the metal component is utilized to convert ethylene into ethane and may also enhance the desorption of coke precursors. The conversion of ethylene into ethane avoids the oligomerization of the olefin to products that may deactivate the catalyst.

In one or more embodiments, the metals are incorporated into the catalyst by ion exchange or impregnation of their salts in aqueous solution. The catalysts with the incorporated metals are then calcined in air and the metals are converted into their oxide forms, which do not present hydrogenation activity. In order to be active for hydrogenation these oxides are converted into metal sulfides, for example metal sulfides of Mo, Ni, or W, or the metal oxides can be reduced to their elemental metal form, for example elemental forms of Mo, Pt, Re, Pd, or Rh. In one or more embodiments, the composite zeolite catalyst is impregnated with rhenium in the form of ammonium perrhenate ($NH_4ReO_4$) as a metal precursor through an incipient wetness procedure. In one or more embodiments, the composite zeolite catalyst is impregnated with molybdenum in the form of ammonium molybdate tetrahydrate (($NH_4)_6Mo_7O_{24} \cdot 4H_2O$) as a metal precursor through an incipient wetness procedure.

In various embodiments, the impregnated metal component may be present in only the MOR-L, only the ZSM-5, or both. For example, the impregnated metal component may be in the MOR-L or ZSM-5 individually from 0.01 to 20.0 wt. %, or from 2 to 5 wt. %, or from 0.1 to 1.5 wt. %, or from 0.25 to 0.5 wt. %, or approximately 0.3 wt. % of the MOR-L or ZSM-5.

In one embodiment, the molar ratio of silicon to aluminum (Si/Al) in the MOR-L is from 4:1 to 10:1. In further embodiments, the molar ratio of silicon to aluminum in the MOR-L is from 5:1 to 8:1 or from 6:1 to 7:1.

The composite zeolite catalyst and the MOR-L and ZSM-5 individual components comprise porosity. A micropore volume and a mesopore volume represent the specific volumes corresponding to the microporous structure and to the mesoporous structure, respectively. The mesopores are mainly due to intercrystalline voids formed, because of the very small size of the zeolite crystals. The pore size ranges for mesopores and micropores are in conformity with conventionally understood size ranges for such pore classifications with micropores representing pores under 2 nanometers (nm) in diameter and mesopores representing pores of 2 to 50 nm in diameter. A total pore volume would additionally include any macropores if present.

From a property standpoint, in one or more embodiments, the MOR-L may have a micropore volume ($V_{micro}$) of at least 0.15 cubic centimeters per gram ($cm^3/g$), or a micropore volume of at least 0.16 cm/g, a micropore volume of 0.15 to 0.25 $cm^3/g$, or a micropore volume of 0.16 to 0.2 $cm^3/g$. The micropore volume may be calculated by the t-plot method of determining micropore volume known to one having skill in the art. Similarly, in one or more embodiments, the MOR-L may have a mesopore volume ($V_{meso}$) of at least 0.15 cubic centimeters per gram ($cm^3/g$), a mesopore volume of at least 0.2 $cm^3/g$, a mesopore volume of 0.15 to 0.3 $cm^3/g$, or a mesopore volume of 0.2 to 0.3 $cm^3/g$. The mesopore volume may be calculated according to the Barrett-Joiner-Halenda (BJH) method of determining mesopore volume known to one having skill in the art. Details regarding the t-plot method and the BJH method of calculating micropore volume and mesopore volume respectively are provided in Galarneau et al., "Validity of the t-plot Method to Assess Microporosity in Hierarchical Micro/Mesoporous Materials", Langmuir 2014, 30, 13266-13274, for example. It is noted that the MOR-L has a higher $V_{meso}$ than commercial MOR (CBV21A) as the layered morphology of MOR-L results in a larger ratio of external to internal surface area.

Regarding the ZSM-5 porosity, the ZSM-5 may have a micropore volume ($V_{micro}$) of at least 0.05 cubic centimeters per gram ($cm^3/g$), or a micropore volume of at least 0.10 cm/g, a micropore volume of 0.05 to 0.25 $cm^3/g$, or a micropore volume of 0.10 to 0.20 $cm^3/g$ in accordance with the t-plot method of determining micropore volume. Similarly, in one or more embodiments, the ZSM-5 may have a mesopore volume ($V_{meso}$) of at least 0.01 cubic centimeters per gram ($cm^3/g$), or a mesopore volume of at least 0.03 $cm^3/g$, a mesopore volume of 0.01 to 0.1 $cm^3/g$, a mesopore volume of 0.03 to 0.08 $cm^3/g$ calculated according to the Barrett-Joiner-Halenda (BJH) method of determining mesopore volume.

The surface area of the pores of the composite zeolite catalyst and the MOR-L and ZSM-5 individually affect the TMB and MEB conversion of the heavy reformate. An increased surface area provides increased interaction between the individual catalyst components and the constituents of the heavy reformate feed allowing for increased conversion activity.

In one or more embodiments, the MOR-L may have a surface area defined by a Brunauer-Emmett-Teller (BET) analysis ($S_{BET}$) of at least 300 square meters per gram ($m^2/g$), a $S_{BET}$ surface area of at least 425 $m^2/g$, or a $S_{BET}$ surface area of at least 450 $m^2/g$. Further, the MOR-L may have a micropore surface area ($S_{micro}$) of 300 $m^2/g$ to 400 $m^2/g$. The micropore surface area may be calculated directly from the micropore volume. Additionally, the zeolite composite catalyst may have an external surface area ($S_{Ext}$) of at least 100 $m^2/g$, 100 to 250 $m^2/g$, 100 to 200 $m^2/g$, or 100 to 175 $m^2/g$. It is noted that the external surface area is obtained as the difference between the BET surface area and the micropore surface area. It is noted that the MOR-L has a higher $S_{Ext}$ than commercial MOR (CBV21A) as the layered morphology of MOR-L results in a larger ratio of external to internal surface area.

In one or more embodiments, the ZSM-5 may have a surface area defined by a Brunauer-Emmett-Teller (BET) analysis ($S_{BET}$) of at least 300 square meters per gram ($m^2/g$), a $S_{BET}$ surface area of at least 325 $m^2/g$, or a $S_{BET}$ surface area of at least 350 $m^2/g$. Further, the ZSM-5 may have a micropore surface area ($S_{micro}$) of 275 $m^2/g$ to 400 $m^2/g$. In one or more embodiments, the ZSM-5 zeolite catalyst is a commercially available ZSM-5. For example, the ZSM-5 may be CBV3024E from Zeolyst International (Conshohocken, Pa. USA).

MOR-L is not a commercially available zeolite catalyst and therefore must be synthesized for utilization in the composite zeolite catalyst. It will be appreciated that various synthesis procedures may be utilized to prepare the MOR-L for utilization in the composite zeolite catalyst. In one embodiment, the synthesis of the MOR-L comprises combining a silicon source and an organic structure directing agent, and an aluminum precursor in a reagent container to form a catalyst gel. The catalyst gel is then heated to form the composite zeolite catalyst particles. One example synthesis procedure is detailed in the Examples section of this disclosure.

EXAMPLES

The described embodiments will be further clarified by the following examples and comparative examples.

The following synthesis procedure for MOR-L serves as an example and differing synthesis procedures may equally be utilized to prepare the MOR-L for utilization in the composite zeolite catalyst.

For demonstration purposes, composite zeolite catalysts and the constituents of the composite zeolite catalysts were prepared in accordance with one or more embodiments of this disclosure. Composite zeolite catalyst particles were synthesized with rhenium incorporated into the catalyst particles. Rhenium was incorporated into the samples at 0.3 wt. % by means of the incipient wetness procedure using ammonium perrhenate ($NH_4ReO_4$) as a metal precursor. The rhenium was incorporated into the MOR-L and ZSM-5 individually and the generated zeolites were then physically mixed in a 60:40 MOR-L:ZSM-5 weight ratio to generate Example 1.

To synthesize MOR-L, 0.177 g of $NaAlO_2$ ($Al_2O_3$ 57.6 wt. %, $Na_2O$ 37.9 wt. % and $H_2O$ 4.5 wt. %) was added to a 3.135 g of a solution of NaOH (10 wt. %). Additionally, 1.087 g of $C_{22-6-6}Br_2$ (molar weight=724.48 g/mol) was added as an organic structure-directing agent. Finally, 3.005 g of Ludox AS-40 (Sigma-Aldrich) was added as a silicon source to form the catalyst gel. The resulting molar composition of the catalyst gel was 0.25 $Na_2O$:1$SiO_2$: 0.05$Al_2O_3$:0.075$C_{22-6-6}Br_2$:40$H_2O$ in conformity with Table 1. The gel with the desired composition was introduced into an autoclave lined with polytetrafluoroethylene at 150° C. under stirring at 60 rpm and autogenous pressure for 5 days. In a final step, the resultant powder from the autoclave was filtered and washed with hot water (50° C.), and dried in an oven at 100° C. overnight. The acid zeolite was obtained by ion exchange with $NH_4Cl$ (2.5M solution at 80° C. for 1 h) and calcined with air flow at 500° C. for 8 hours.

TABLE 1

Gel Composition

| Sample | Composition |
|---|---|
| MOR-L (Si/Al = 6.5) | 0.25 $Na_2O$:1 $SiO_2$:0.05 $Al_2O_3$:0.075 $C_{22\text{-}6\text{-}6}Br_2$:40 $H_2O$ |

For demonstration purposes, a composite zeolite catalyst was prepared in accordance with one or more embodiments of this disclosure. The composite zeolite catalyst was formed as a physical mixture of rhenium containing MOR-L and rhenium containing ZSM-5. Pure MOR-L and pure ZSM-5 zeolites were impregnated with rhenium. Rhenium was incorporated into each sample at 0.3 wt. % by means of the incipient wetness procedure using ammonium perrhenate ($NH_4ReO_4$) as a metal precursor. After rhenium loading, the samples were stored in a desiccator for at least 5 hours and then dried at 100° C. overnight. The rhenium loaded MOR-L and ZSM-5 were mixed in a 60:40 weight ratio of MOR-L:ZSM-5. The ZSM-5 was the commercially available CBV3024E (Zeolyst International). The physical mixture was calcined in a fixed bed reactor with the temperature increased up to 500° C. in a flow of nitrogen gas ($N_2$) at 100 milliliter per minute (ml/min) and then maintained at 500° C. for 3 hours under air flow at 100 ml/min. The sample was then cooled to room temperature or reduction temperature under a nitrogen flow at 100 ml/min. The prepared composite zeolite catalyst with a 60:40 weight ratio of Re/MOR-L:Re/ZSM-5 is designated as Example 1. Pure generated MOR-L was designated as Example 2 (comparative) and the rhenium impregnated MOR-L was designated as Example 3 (comparative).

Comparative zeolite catalyst samples were also prepared for comparison with the composite zeolite catalyst particles. ATA-21 (Comparative Example 4) represents a commercial catalyst based on a physical mixture of Mordenite and ZSM-5, CBV21A (Zeolyst International) represents commercially available Mordenite (Comparative Example 5), and CBV3024E (Zeoyst International) represents commercially available ZSM-5 (Comparative Example 6). Samples of the commercially available pure MOR and ZSM-5 were also prepared with rhenium incorporated into each catalyst. As with the composite zeolite catalyst, rhenium was incorporated into each sample. The CBV21A (commercially available MOR) with incorporated rhenium was designated as Comparative Example 7, and the CBV3024E (commercially available ZSM-5) with incorporated rhenium was designated as Comparative Example 8. Rhenium was incorporated into all of the samples at 0.3 wt. % by means of the incipient wetness procedure using ammonium perrhenate ($NH_4ReO_4$) as a metal precursor. Rhenium containing CBV21A and rhenium containing CBV3024E were also mixed in a 60:40 weight ratio MOR:ZSM-5, and designated as Comparative Example 9.

A listing of the composition of each Example is provided in Table 2.

TABLE 2

Composition of each Example

| EXAMPLE | COMPOSITION |
|---|---|
| Example 1 | 60 wt. % MOR-L with 0.3 wt. % rhenium and 40 wt. % ZSM-5 with 0.3 wt. % rhenium |
| Comparative Example 2 | MOR-L |
| Comparative Example 3 | MOR-L with 0.3 wt. % rhenium |
| Comparative Example 4 | ATA-21 |
| Comparative Example 5 | CBV21A (Commercial Mordenite, MOR) |
| Comparative Example 6 | CBV3024E (Commercially ZSM-5) |
| Comparative Example 7 | CBV21A with 0.3 wt. % rhenium |
| Comparative Example 8 | CBV3024E with 0.3 wt. % rhenium |
| Comparative Example 9 | 60 wt. % CBV21A with 0.3 wt. % rhenium and 40 wt. % ZSM-5 with 0.3 wt. % rhenium |

The physico-chemical properties of each of the samples were quantified. Specifically, the silicon to aluminum ratio as well as the final wt. % of Re in each sample was determined for each sample type. Additionally, the micropore volume and the mesopore volume were calculated according to the t-plot method and the BJH correlation method respectively. Further, the micropore surface area was calculated from the micropore volume, the total specific surface area was calculated in accordance with the Brunauer-Emmett-Teller method widely used for evaluating the surface area of porous and finely-divided materials, and the external surface area was calculated based on the difference between the total specific surface area and the micropore surface area. These physio-chemical properties are delineated in Table 3.

TABLE 3

Chemical composition and textural properties of samples

| Sample | Si/Al | Re (wt. %) | $S_{BET}$ ($m^2$/g) | $S_{micro}$ ($m^2$/g) | $S_{Ext}$ ($m^2$/g) | $V_{micro}$ ($cm^3$/g) | $V_{meso}$ ($cm^3$/g) |
|---|---|---|---|---|---|---|---|
| Comp. Example 5 (MOR) | 10.1 | — | 451 | 425 | 26 | 0.204 | 0.029 |
| Comp. Example 7 (Rhenium MOR) | 8.9 | 0.3 | 429 | 408 | 21 | 0.200 | 0.027 |
| Comp. Example 2 (MOR-L) | 6.5 | — | 499 | 331 | 168 | 0.162 | 0.238 |
| Comp. Example 3 (Rhenium MOR-L) | 6.1 | 0.3 | 470 | 357 | 113 | 0.174 | 0.152 |
| Comp. Example 6 (ZSM-5) | 13.0 | — | 372 | 332 | 40 | 0.162 | 0.055 |
| Comp. Example 8 (Rhenium ZSM-5) | 13.4 | 0.3 | 365 | 327 | 39 | 0.159 | 0.054 |

Table 3 illustrates that the MOR-L and MOR have differing properties which may have a direct effect on the catalytic behavior of a composite zeolite catalyst formed from each one respectively. It is initially noted that the Si/Al molar ratio of MOR-L is lower than that of the MOR. Additionally, the MOR-L comprises a greater external surface area and a greater mesopore volume. The greater $S_{ext}$ and $V_{meso}$ is attributed to the layered morphology of MOR-L which results in a greater ratio of external to internal surface area of the formed crystals when compared to MOR The acidic properties of each of the samples were also quantified. Acidity measurements were carried out by adsorption/desorption of pyridine followed by IR spectroscopy. Self-supported wafers (10 milligrams per centimeter squared (mg $cm^{-2}$)) of calcined samples, previously activated at 400° C. and $10^{-2}$ Pascal (Pa) overnight in a Pyrex vacuum cell, were allowed to come in contact with $6.5 \times 10^2$ Pa of pyridine vapor at room temperature and desorbed in vacuum at increasing temperatures (150° C., 250° C., and 250° C.). The spectra were recorded at room temperature.

All the spectra were scaled according to the sample weight. Brønsted and Lewis acidity of the samples compared are given in arbitrary units, according to the intensity of the bands assigned to the pyridine interacting with the Brønsted and Lewis acid sites of the zeolites (1550 and 1450 cm$^{-1}$, respectively). These acidic properties are listed in Table 4.

TABLE 4

Acidic properties of samples

| Sample | Bronsted Acidity (u.a.) | | | | Lewis Acidity (u.a.) | | |
|---|---|---|---|---|---|---|---|
| | B150 | B250 | B350 | B350/B250 | L150 | L250 | L350 |
| Comp. Example 5 (MOR) | 618 | 487 | 373 | 0.48 | 51 | — | — |
| Comp. Example 7 (Rhenium MOR) | 400 | 363 | 299 | 0.75 | 65 | — | — |
| Comp. Example 2 (MOR-L) | 369 | 278 | 180 | 0.49 | 125 | — | — |
| Comp. Example 3 (Rhenium MOR-L) | 312 | 274 | 192 | 0.62 | 108 | — | — |
| Comp. Example 6 (ZSM-5) | 439 | 395 | 337 | 0.77 | 51 | 36 | 32 |
| Comp. Example 8 (Rhenium ZSM-5) | 411 | 336 | 293 | 0.71 | 94 | 68 | 61 |

Figure 4:
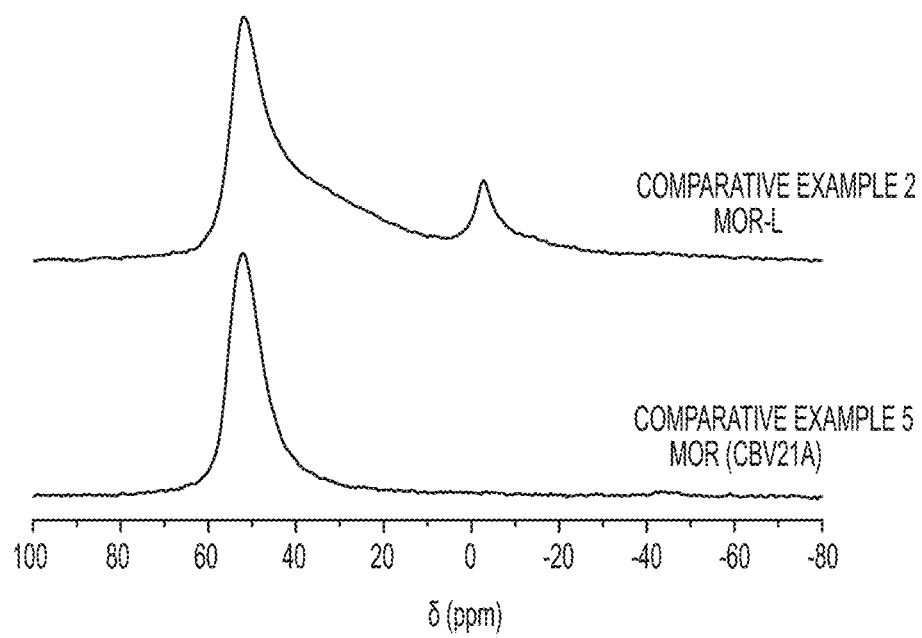
FIG. 4 is a $^{27}$Al-NMR spectra for MOR-L and a commercially available Mordenite.

Table 4 illustrates that MOR-L (Comparative Examples 2 and 3) presents a lower Brønsted acid density and higher number of Lewis acid sites in comparison with MOR (Comparative Examples 5 and 7). The difference in Brønsted acid site density and number of Lewis acid sites may be attributed to the presence of extraframework Aluminum (EFAL) with part of the EFAL generating more Lewis acid sites while neutralizing bridging hydroxyl groups, thereby decreasing the Brønsted acid density. With reference to FIG. 4, enclosing the $^{27}$Al-NMR spectra, the EFAL in Comparative Example 2 (MOR-L) is indicated by the extra band appearing at a chemical shift close to −3 parts per million (ppm). It is noted that no band is indicated for Comparative Example 5 (MOR).

Figure 5:
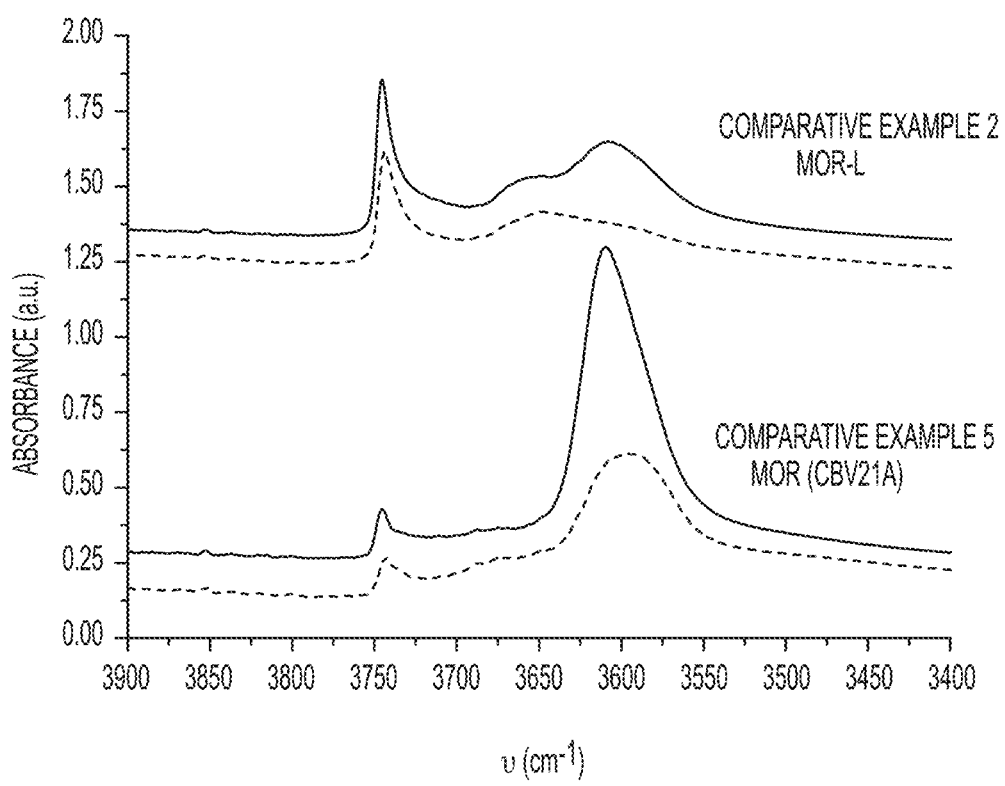
FIG. 5 is a Fourier Transform Infrared (FT-IR) spectra of commercially available Mordenite and MOR-L.

With reference to FIG. 5, enclosing the Fourier transformed infrared spectra, the bands from Comparative Example 2 (MOR-L) and Comparative Example 5 (MOR) may be compared. The spectra for both before pyridine adsorption (represented as a solid line) and after pyridine adsorption at 150° C. (represented as a dotted line) are presented. It is noted that Comparative Example 2 (MOR-L) presents a more intense band at 3745 cm$^{-1}$ than Example 5 (MOR), the band corresponding to external SiOH which is in agreement with the higher external surface area. Further, comparing the band at 3600 cm$^{-1}$, which corresponds to the acid hydroxyls, it may be concluded that most of the acid sites of Comparative Example 2 (MOR-L) sample are able to interact with the basic probe molecule, while conversely only a portion of the Brønsted acid sites for Comparative Example 5 (MOR) are accessible to pyridine. Finally, comparing the band at 3680 cm$^{-1}$, which corresponds to external extraframework Al species, it may be concluded that Comparative Example 2 (MOR-L) comprises the EFAL, whereas Comparative Example 5 (MOR) does not.

As stated previously, the present composite zeolite catalyst represent a dealkylation and transalkylation catalyst suitable for converting $C_{9+}$ alkyl aromatic hydrocarbons to a product stream comprising benzene, toluene, and xylenes, particularly to commercially valuable xylenes. The feed stream to the conversion process generally comprises alkylaromatic hydrocarbons in the carbon number range $C_9$ to $C_{11+}$ that may include, for example, such hydrocarbons as propylbenzenes, methylethylbenzenes, tetramethylbenzenes, ethyldimethylbenzenes, diethylbenzenes, methylpropylbenzenes, and mixtures thereof. For purposes of testing and quantifying the examples and comparative examples a simulated heavy reformate feed was generated. The simulated heavy reformate feed comprises 30 wt. % para-methylethylbenzene (p-MEB) and 70 wt. % 1,2,4-trimethylbenzene (1,2,4-TMB).

Catalytic test for conversion of the simulated heavy reformate feed were performed in a reaction system comprising sixteen (16) continuous fixed-bed parallel microreactors. Each reactor was capable of being fed independently with the desired flow of the simulated reformate feed and $H_2$ making it possible to operate in a wide range of contact times and hydrogen/hydrocarbon molar ratios. The simultaneous catalytic experiments were carried out under the following conditions: 20 bar total pressure, a hydrogen/hydrocarbon molar ratio of 8.5, a reaction time of 16 hours per temperature, and a weight hourly space velocity (WHSV) of 10 inverse hours (h$^{-1}$). After the testing at each temperature the zeolitic catalysts were kept at that temperature and under $H_2$ atmosphere for an additional 10 hours. Each zeolitic catalyst sample was prepared to a particle size of 0.2 to 0.4 millimeters (mm). The tested zeolitic samples included Example 1 (60:40 weight ratio MOR-L:ZSM-5 with 0.3 wt. % rhenium), Comparative Example 4 (ATA-21), Comparative Example 3 (MOR-L with 0.3 wt. % rhenium), Comparative Example 7 (MOR with 0.3 wt. % rhenium) and Comparative Example 9 (60 wt. % CBV21A with 0.3 wt. % rhenium and 40 wt. % ZSM-5 with 0.3 wt. % rhenium). Comparative Example 4 (ATA-21) is a commercially available heavy reformate conversion catalyst based on a physical mixture of Mordenite and ZSM-5 zeolites and serves as a comparative example for the composite zeolite catalysts comprising MOR-L and ZSM-5. Similarly, Comparative Example 7 (MOR with 0.3 wt. % rhenium) is a commercially available Mordenite zeolite (CBV21A) and serves as a comparative example for the composite zeolite catalysts comprising MOR-L with 0.3 wt. % rhenium (Comparative Example 3), which further serves as a comparative example for the composite zeolite catalysts comprising rhenium containing MOR-L and ZSM-5 and the synergistic effect of both components. Finally, Comparative Example 9 is a physical mixture of 60 wt % rhenium loaded commercial CBV21A and 40 wt % rhenium loaded CBV3024E, and serves as a comparative example for the composite zeolite catalysts comprising rhenium containing MOR-L and ZSM-5.

Each fixed-bed microreactor reactor was prepared with 125 mg of the zeolitic catalyst sample and diluted with silicon carbide (SiC) to a total bed volume of 2.0 ml for testing. The experiments were performed on the same zeolite weight basis so in Comparative Example 4 (ATA-21) the amount of catalyst added was adjusted according to its zeolite content in order to have 125 mg of zeolite excluding the matrix. Four consecutive reactions phases were completed at temperatures of 350° C., 375° C., 400° C., and a return to 350° C.

The reaction products from each of the fixed-bed microreactors were analyzed by on-line gas chromatography using two independent channels (Bruker 450 Gas Chromatograph). Argon (Ar) as an internal standard, $H_2$, methane, and ethane were analyzed in a first channel equipped with a thermal conductivity detector (TCD) and three columns. The three columns were a Hayesep N pre-column (0.5 m length)

(Hayes Separations, Inc.), a Hayesep Q (1.5 m length) (Hayes Separations, Inc.), and a 13× molecular sieve (1.2 m length). In a second channel the $C_1$-$C_4$ hydrocarbons were first separated from the aromatics in a CP-Wax capillary column (5.0 m length and 0.32 mm inner diameter) (Cole-Parmer). Subsequently, the $C_1$-$C_4$ gases were separated in a column with CP-PoraBOND Q (25 m length and 0.32 mm inner diameter) (Cole-Parmer) and detected in a flame ionization detector (FID). Separation of the aromatics was completed in a second CP-Wax (1.0 m length and 0.32 mm inner diameter) connected to a second FID.

Figure 6:
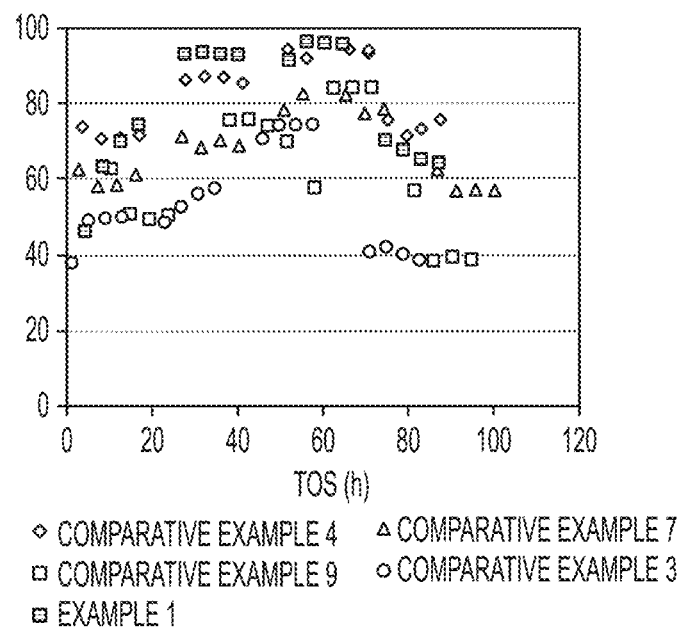
FIG. 6 is a graph of Methylethylbenzene (MEB) conversion of a simulated heavy reformate stream obtained with commercially available zeolite catalysts, MOR-L impregnated with 0.3 weight percent (wt. %) rhenium, and a composite zeolite catalyst in accordance with one or more embodiments of the present disclosure.
Figure 7:
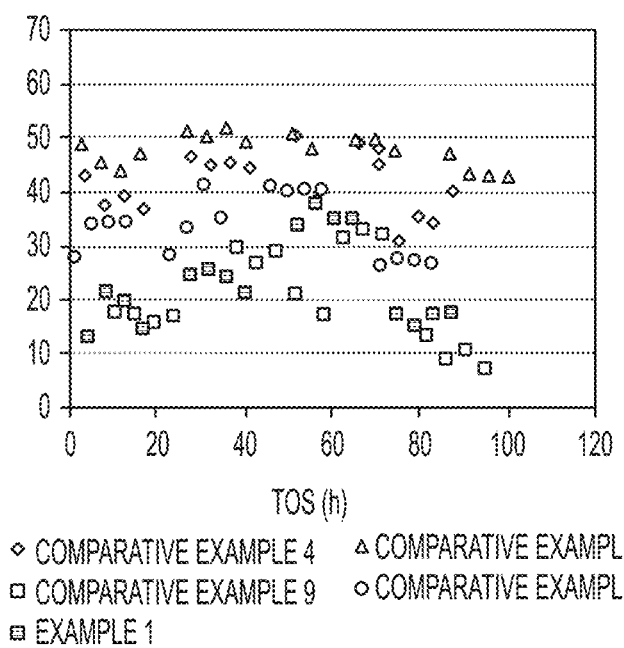
FIG. 7 is a graph of Trimethylbenzene (TMB) conversion of a simulated heavy reformate stream obtained with commercially available zeolite catalysts, MOR-L impregnated with 0.3 wt. % rhenium, and a composite zeolite catalyst in accordance with one or more embodiments of the present disclosure.
Figure 8:
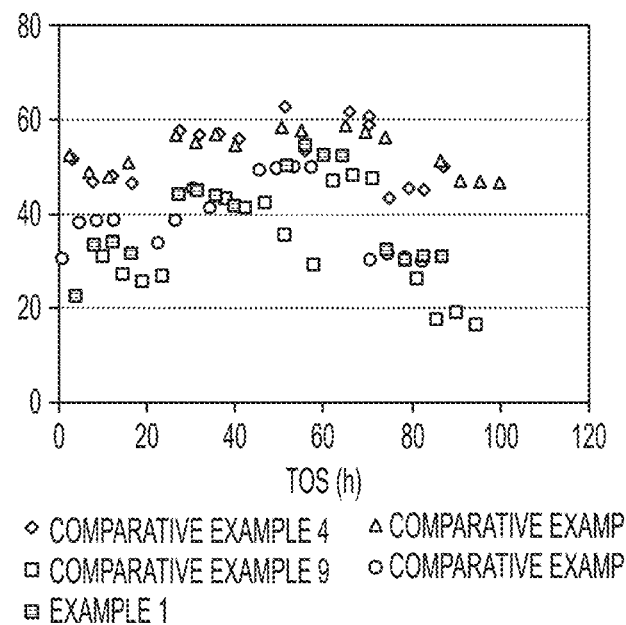
FIG. 8 is a graph of overall conversion (MEB+TMB) of a simulated heavy reformate stream obtained with commercially available zeolite catalysts, MOR-L impregnated with 0.3 wt. % rhenium, and a composite zeolite catalyst in accordance with one or more embodiments of the present disclosure.
Figure 9:
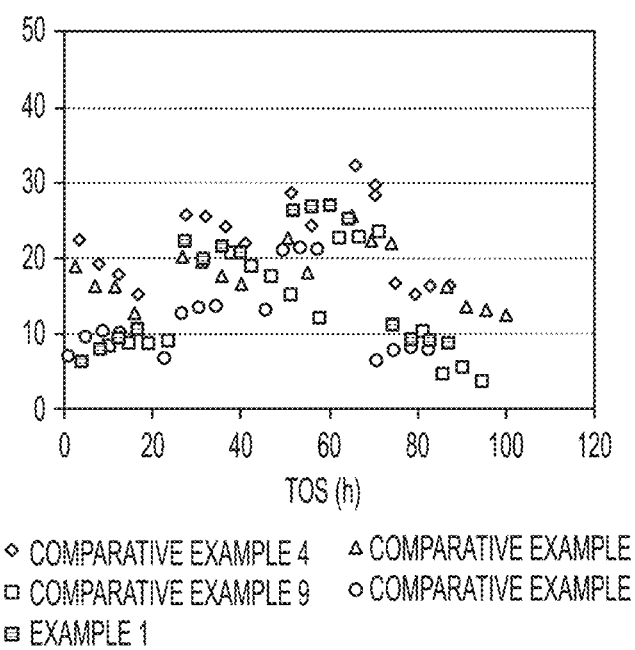
FIG. 9 is a graph of xylenes yield from a simulated heavy reformate stream obtained with commercially available zeolite catalysts, MOR-L impregnated with 0.3 wt. % rhenium, and a composite zeolite catalyst in accordance with one or more embodiments of the present disclosure.
Figure 10:
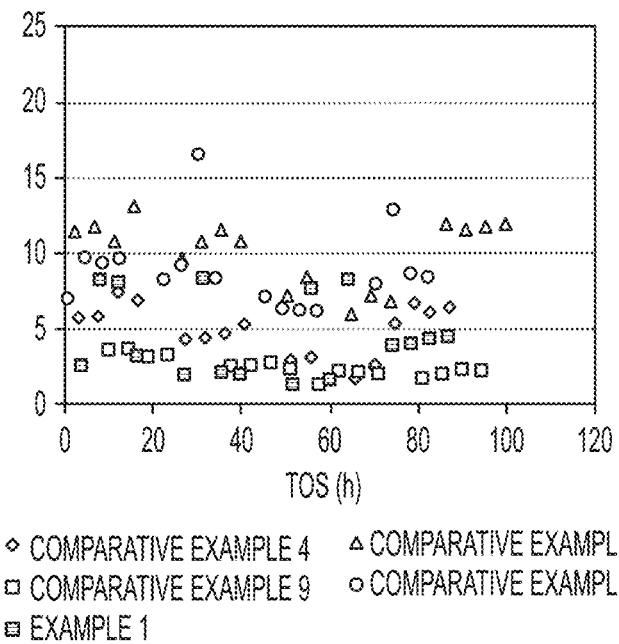
FIG. 10 is a graph of $A_{10}$ yield (yield of aromatics with 10 carbons) from a simulated heavy reformate stream obtained with commercially available zeolite catalysts, MOR-L impregnated with 0.3 wt. % rhenium, and a composite zeolite catalyst in accordance with one or more embodiments of the present disclosure.

With reference to FIGS. 6, 7 and 8, the MEB conversion (dealkylation), TMB conversion (transalkylation), and overall conversion (MEB+TMB) are illustrated for each of Example 1, Comparative Example 3, Comparative Example 4, comparative Example 7, and Comparative Example 9 versus time on stream (TOS). It is noted that Example 1 did not exhibit deactivation during the testing procedure. This phenomenon is indicated by the conversion percentage for the initial 350° C. stage at the beginning of each test and the final 350° C. stage at the conclusion of each test being similar.

The lack of deactivation observed for the composite zeolite catalyst is believed to be due to its higher catalytic efficiency, which reduces the formation of heavy alkylaromatics. The proximity of the two zeolite phases (ZSM-5 and MOR-L) because of the physical mixture of the two zeolite phases in a single catalyst and reactor allows the TMB present in the feed to preferentially react on the MOR-L crystals with the toluene previously formed by dealkylation of MEB on the ZSM-5 crystals. In fact, the overall conversion obtained with Example 1 is higher than the one obtained with Comparative Example 3, based on pure MOR-L with no ZSM-5, due to a lower in-situ production of toluene. Additionally, the layered morphology of the MOR-L crystals creates short diffusion pathways which allow the products to diffuse out of the zeolite crystals before undergoing reactions into heavier aromatics, coke precursors, or both. This reduced formation of $A_{10+}$ and coke precursors leads to improved catalyst life.

Figure 11:
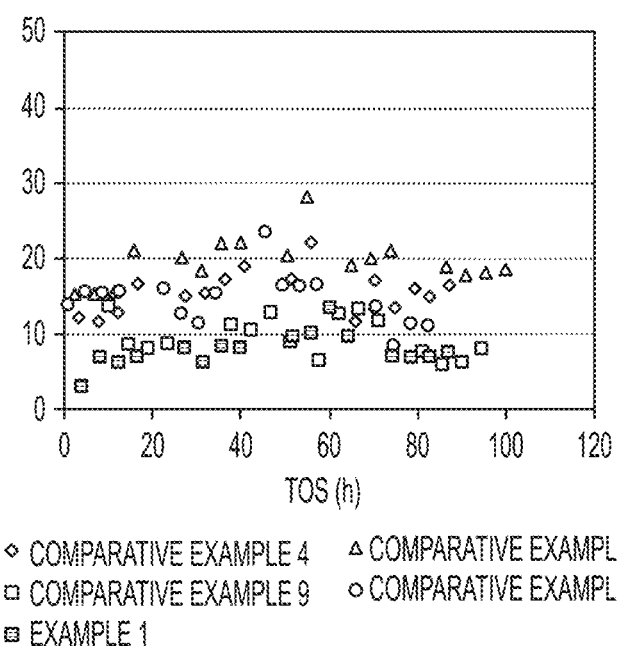
FIG. 11 is a graph of $A_{10+}$ yield (yield of aromatics with more than 10 carbons) from a simulated heavy reformate stream obtained with commercially available zeolite catalysts, MOR-L impregnated with 0.3 wt. % rhenium, and a composite zeolite catalyst in accordance with one or more embodiments of the present disclosure.
Figure 12:
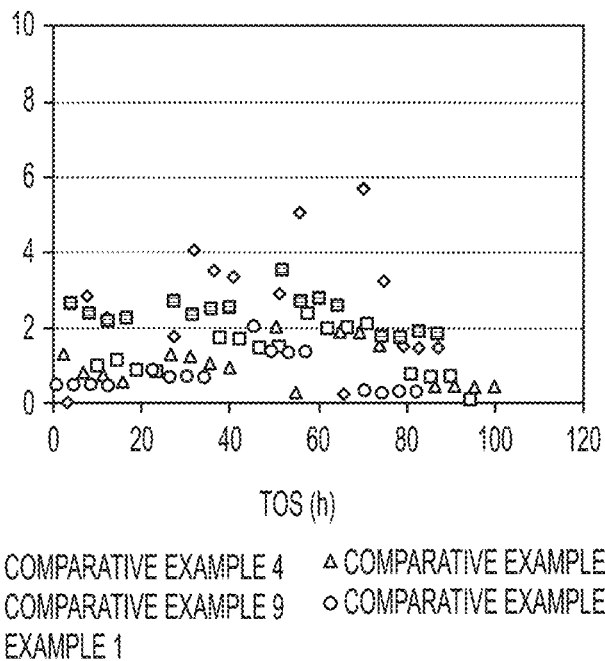
FIG. 12 is a graph of light hydrocarbon yield from a simulated heavy reformate stream obtained with commercially available zeolite catalysts, MOR-L impregnated with 0.3 wt. % rhenium, and a composite zeolite catalyst in accordance with one or more embodiments of the present disclosure.
Figure 13:
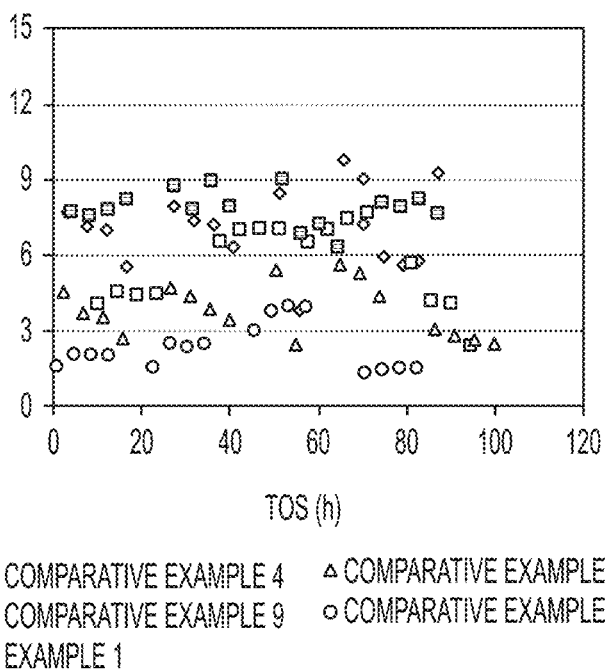
FIG. 13 is a graph of toluene yield from a simulated heavy reformate stream obtained with commercially available zeolite catalysts, MOR-L impregnated with 0.3 wt. % rhenium, and a composite zeolite catalyst in accordance with one or more embodiments of the present disclosure.
Figure 14:
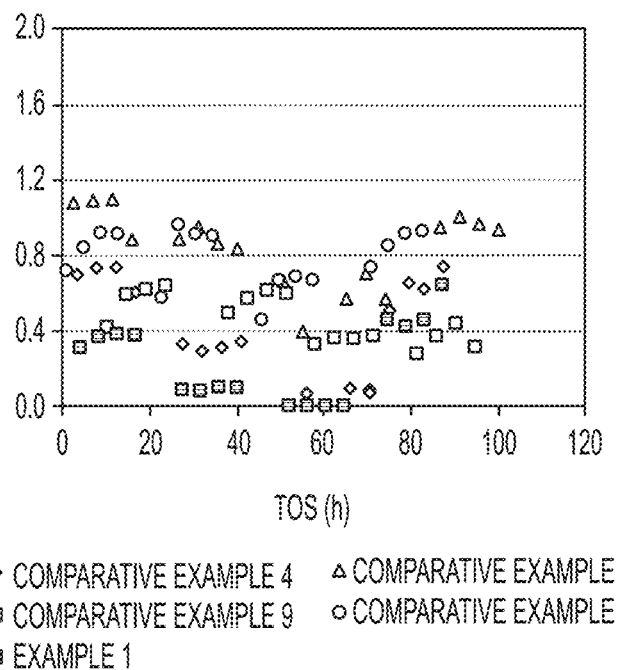
FIG. 14 is a graph of ethylbenzene yield from a simulated heavy reformate stream obtained with commercially available zeolite catalysts, MOR-L impregnated with 0.3 wt. % rhenium, and a composite zeolite catalyst in accordance with one or more embodiments of the present disclosure.
Figure 15:
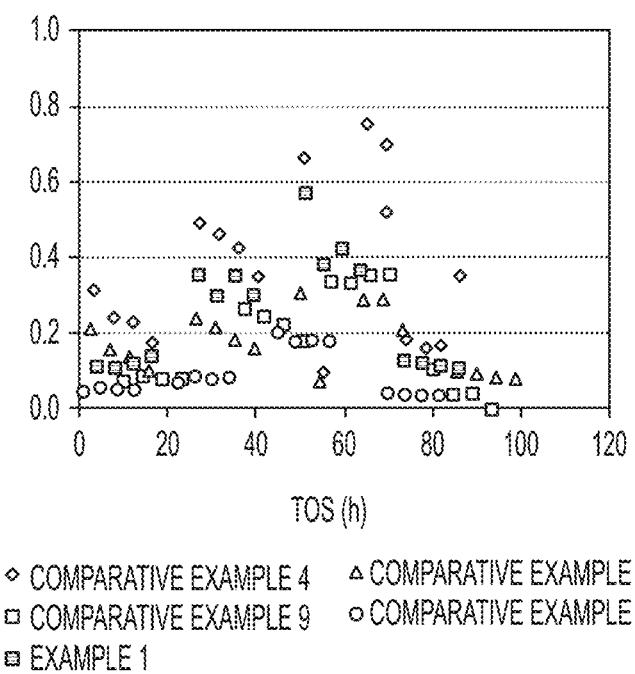
FIG. 15 is a graph of benzene yield from a simulated heavy reformate stream obtained with commercially available zeolite catalysts, MOR-L impregnated with 0.3 wt. % rhenium, and a composite zeolite catalyst in accordance with one or more embodiments of the present disclosure.

With reference to FIGS. 9, 10, 11, 12, 13, 14 and 15, the xylenes yield, $A_{10}$ yield, $A_{10+}$ yield, light hydrocarbon yield, toluene yield, ethylbenzene yield, and benzene yield are respectively illustrated for each of the 5 sample types versus TOS. It is noted that Example 1 (60:40 weight ratio MOR-L:ZSM-5 with 0.3 wt. % rhenium) favors the xylenes production as compared to Comparative Example 3 (MOR-L with 0.3 wt. % rhenium), and Comparative Example 9 (60 wt. % CBV21A with 0.3 wt. % rhenium+40 wt. % CBV3024E with 0.3 wt. % rhenium). The higher selectivity to xylenes is believed a consequence of the lower production of undesirable $A_{10+}$ aromatics. As indicated in FIG. 11, Example 1 (60:40 weight ratio MOR-L:ZSM-5 with 0.3 wt. % rhenium) demonstrated the lowest yield of $A_{10+}$ aromatics.

The results generated from testing the samples with the simulated heavy reformate provided information regarding the relative activity of the different catalyst compositions and their stability towards deactivation with an extended TOS. The catalysts were also tested under conditions closer to industrial conditions which would be observed for conversion of heavy reformate to xylenes. To more accurately reflect industrial conditions a supply of actual industrial heavy reformate with known composition was utilized. Table 5 delineates the composition of the industrial heavy reformate used for testing and Table 6 provides the relative ratios of various components.

TABLE 5

Industrial Heavy Reformate Composition

| Hydrocarbon Type | Hydrocarbon Sub-Type | | Mass % |
|---|---|---|---|
| $A_8$ | Total | | 3.94 |
| | Ethylbenzene | | 0.03 |
| | p-xylene | | 0.15 |
| | m-xylene | | 0.38 |
| | o-xylene | | 3.38 |
| $A_9$ | Total | | 82.75 |
| | Isopropylbenzene | Total | 0.43 |
| | n-propylbenzene | Total | 2.07 |
| | Methylethylbenzene | Total | 19.62 |
| | (MEB) | m- and p-MEB | 15.33 |
| | | o-MEB | 4.29 |
| | Trimethylbenzene | Total | 60.63 |
| | (TMB) | 1,3,5-TMB | 11.69 |
| | | 1,2,4-TMB | 40.81 |
| | | 1,2,3-TMB | 8.13 |
| $A_{10+}$ | Total | | 13.33 |

TABLE 6

Industrial Heavy Reformate Composition Ratio

| $A_8$ | |
|---|---|
| Ethylbenzene:Total $A_8$ | 0.0076 |
| p-xylene:Total $A_8$ | 0.038 |
| m-xylene:Total $A_8$ | 0.096 |
| o-xylene:Total $A_8$ | 0.858 |
| $A_9$ | |
| Isopropylbenzene:Total $A_9$ | 0.0052 |
| n-propylbenzene:Total $A_9$ | 0.025 |
| Total Methylethylbenzene (MEB):Total $A_9$ | 0.237 |
| m- and p-MEB:Total $A_9$ | 0.185 |
| o-MEB:Total $A_9$ | 0.052 |
| m- and p-MEB:Total MEB | 0.781 |
| o-MEB:Total MEB | 0.219 |
| Total Trimethylbenzene (TMB):Total $A_9$ | 0.733 |
| 1,3,5-TMB:Total $A_9$ | 0.141 |
| 1,2,4-TMB:Total $A_9$ | 0.493 |
| 1,2,3-TMB:Total $A_9$ | 0.098 |
| 1,3,5-TMB:Total TMB | 0.193 |
| 1,2,4-TMB:Total TMB | 0.673 |
| 1,2,3-TMB:Total TMB | 0.124 |
| Total $A_9$:Total $A_{10+}$ | 6.21 |

Catalytic tests for conversion of the industrial heavy reformate feed were performed in a fixed-bed stainless-steel tubular reactor. The reactor had a 10.5 mm internal diameter and a 20 centimeter (cm) length. The catalytic experiments in the fixed-bed tubular reactor were carried out under the following conditions: 20 bar total pressure, a hydrogen/hydrocarbon molar ratio of 4:1, a reaction time of 3 hours at each reaction temperature, and a weight hourly space velocity (WHSV) of 10 h$^{-1}$. The reactor was charged with 0.75 grams (g) of catalyst with a particle size of 0.2 to 0.4 mm for each test. The tested zeolitic samples included Example 1 (60:40 weight ratio MOR-L:ZSM-5 with 0.3 wt. % rhenium). Comparative Example 4 (ATA-21), Comparative Example 3 (MOR-L with 0.3 wt. % rhenium), Comparative Example 7 (MOR with 0.3 wt. % rhenium), and Comparative Example 9 (60 wt. % CBV21A with 0.3 wt. % rhenium and 40 wt. % ZSM-5 with 0.3 wt. % rhenium). The catalyst was diluted with SiC to bring the total volume up to a total bed volume of 5.0 ml. For Comparative Example 4 (ATA-21), the amount of catalyst added was adjusted according to its zeolite content in order to have 0.75 g of zeolite (the matrix was excluded). Gaseous compounds (H$_2$, N$_2$) were fed into the system by mass flow meters via a vaporizer. Nitrogen was also fed into the system as an internal reference. The industrial heavy reformate was fed by means of a high performance liquid chromatography (HPLC) pump to the vaporizer. The vaporizer was operated at 300° C. and provided a steady and non-pulsing flow of reactants to the reactor. Prior to commencing the catalytic test, the catalyst was reduced in situ at 450° C. for 1 h under H$_2$ flow (50 ml/min) at atmospheric pressure. For the catalytic testing, four consecutive reactions phases were completed at temperatures of 350° C. (7 h reaction), 375° C. (5 h reaction), 400° C. (5 h reaction), and a return to 350° C. (5 h reaction).

During reaction, the effluent stream was analyzed on-line at intervals of 32 minutes (min) in a Scion 456 Gas Chromatograph equipped with two detection channels. Nitrogen (N$_2$) as an internal standard, H$_2$, methane, and ethane were analyzed in a first channel equipped with a TCD and three columns. The three columns were a Hayesep N pre-column (0.6 m length) (Hayes Separations, Inc.), a Hayesep Q (1.6 m length) (Hayes Separations, Inc.), and a 13× molecular sieve (1.2 m length). In a second channel the C$_1$-C$_4$ hydrocarbons were first separated from the aromatics in a CP-Wax capillary column (5.0 m length and 0.32 mm inner diameter) (Cole-Parmer). Subsequently, the C$_1$-C$_4$ gases were separated in a column with CP-PoraBOND Q (25 m length and 0.32 mm inner diameter) (Cole-Parmer) and detected in a flame ionization detector (FID). Separation of the aromatics was completed in a second CP-Wax (39.5 m length and 0.32 mm inner diameter) connected to a second FID.

Figure 16:
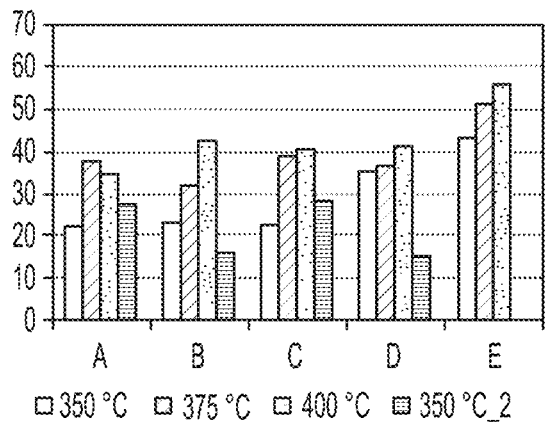
FIG. 16 is a graph of TMB conversion of an industrial heavy reformate stream obtained with commercially available zeolite catalysts, MOR-L impregnated with 0.3 wt. % rhenium, and a composite zeolite catalyst in accordance with one or more embodiments of the present disclosure.
Figure 17:
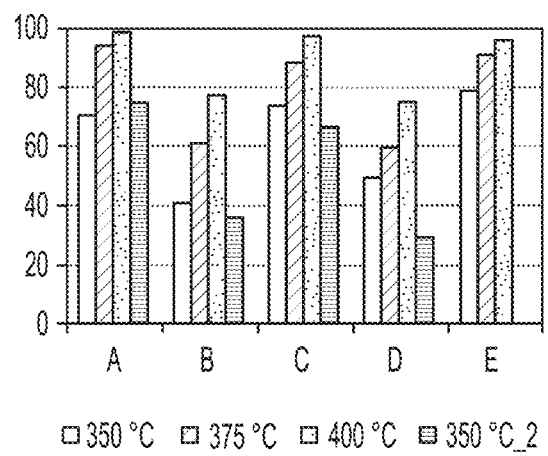
FIG. 17 is a graph of MEB conversion of an industrial heavy reformate stream obtained with commercially available zeolite catalysts, MOR-L impregnated with 0.3 wt. % rhenium, and a composite zeolite catalyst in accordance with one or more embodiments of the present disclosure.
Figure 18:
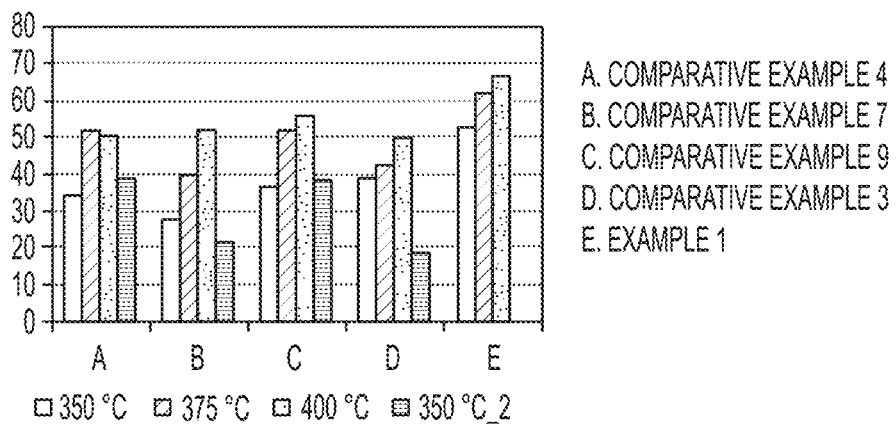
FIG. 18 is a graph of overall conversion of an industrial heavy reformate stream obtained with commercially available zeolite catalysts, MOR-L impregnated with 0.3 wt. % rhenium, and a composite zeolite catalyst in accordance with one or more embodiments of the present disclosure.
Figure 19:
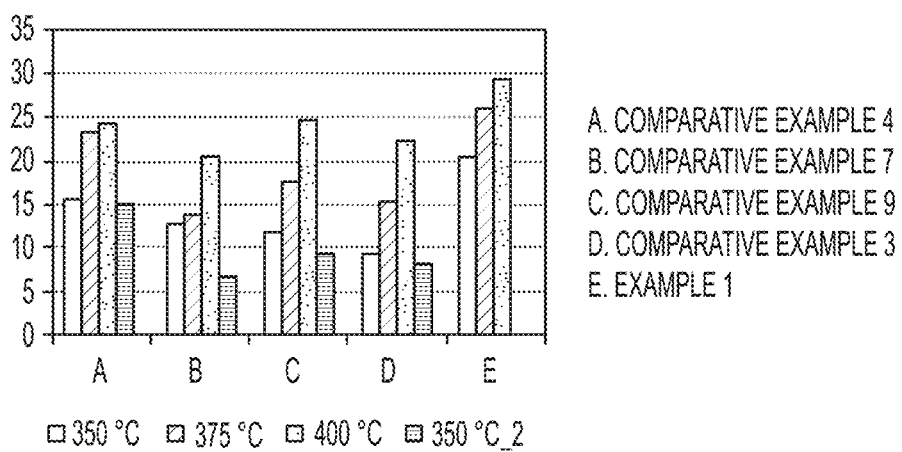
FIG. 19 is a graph of xylenes yield from an industrial heavy reformate stream obtained with commercially available zeolite catalysts, MOR-L impregnated with 0.3 wt. % rhenium, and a composite zeolite catalyst in accordance with one or more embodiments of the present disclosure.
Figure 20:
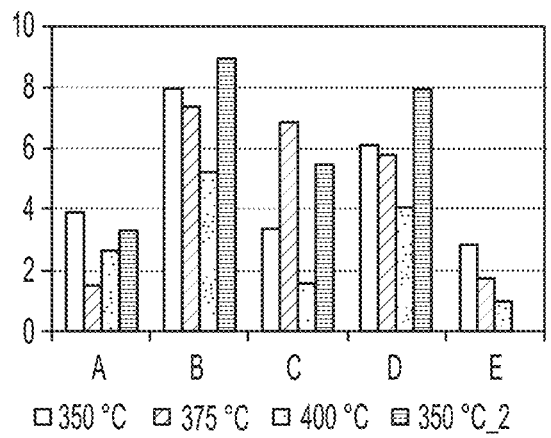
FIG. 20 is a graph of $A_{10}$ yield from an industrial heavy reformate stream obtained with commercially available zeolite catalysts, MOR-L impregnated with 0.3 wt. % rhenium, and a composite zeolite catalyst in accordance with one or more embodiments of the present disclosure.

With reference to FIGS. 16, 17 and 18, the TMB conversion (transalkylation), MEB conversion (dealkylation), and overall conversion (MEB+TMB) are respectively illustrated for each of Example 1, Comparative Example 3, Comparative Example 4, Comparative Example 7, and Comparative Example 9. It is noted that Example 1 (60:40 weight ratio MOR-L:ZSM-5 with 0.3 wt. % rhenium) demonstrated greater overall conversion than the Comparative Examples which is attributed to the greater TMB conversion activity. The individual TMB conversion percentages and MEB conversion percentages are provided in Table 7.

TABLE 7

TMB, MEB, and Overall Conversion

| Catalyst | Temperature | TMB Conversion (%) | MEB Conversion (%) | Overall Conversion (%) |
|---|---|---|---|---|
| Example 1 | 350° C. | 43.12 | 79.36 | 52.85 |
| (60:40 weight ratio MOR-L:ZSM-5 with 0.3 wt. % rhenium) | 375° C. | 51.25 | 91.38 | 62.03 |
|  | 400° C. | 55.81 | 96.32 | 66.69 |
| Comparative Example 3 | 350° C. | 35.26 | 49.43 | 39.00 |
| (MOR-L with 0.3 wt. % rhenium) | 375° C. | 36.54 | 59.55 | 42.62 |
|  | 400° C. | 41.28 | 75.06 | 50.21 |
|  | 350° C. (Return) | 15.15 | 29.00 | 18.81 |
| Comparative Example 4 | 350° C. | 22.22 | 70.53 | 34.18 |
| (ATA-21) | 375° C. | 37.64 | 94.12 | 51.62 |
|  | 400° C. | 34.62 | 98.72 | 50.48 |
|  | 350° C. (Return) | 27.44 | 74.76 | 39.15 |
| Comparative Example 7 | 350° C. | 23.08 | 40.81 | 27.76 |
| (MOR with 0.3 wt. % rhenium) | 375° C. | 31.92 | 61.07 | 39.62 |
|  | 400° C. | 42.55 | 77.44 | 51.77 |
|  | 350° C. (Return) | 15.89 | 35.84 | 21.16 |
| Comparative Example 9 | 350° C. | 22.51 | 73.84 | 36.08 |
| (60:40 weight ratio MOR-:ZSM-5 with 0.3 wt. % rhenium) | 375° C. | 38.86 | 88.46 | 51.96 |
|  | 400° C. | 40.50 | 97.49 | 55.56 |
|  | 350° C. (Return) | 28.19 | 66.55 | 38.32 |

Figure 21:
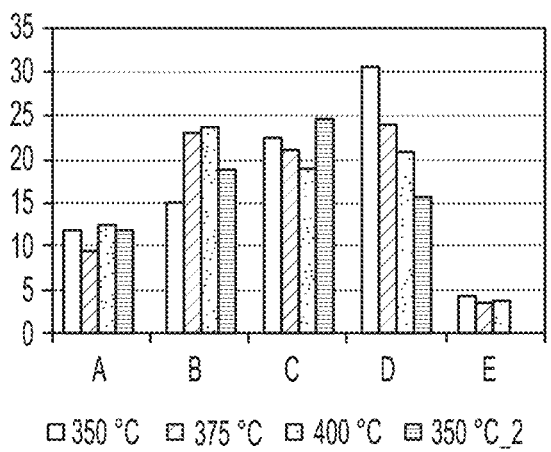
FIG. 21 is a graph of $A_{10+}$ yield from an industrial heavy reformate stream obtained with commercially available zeolite catalysts, MOR-L impregnated with 0.3 wt. % rhenium, and a composite zeolite catalyst in accordance with one or more embodiments of the present disclosure.
Figure 22:
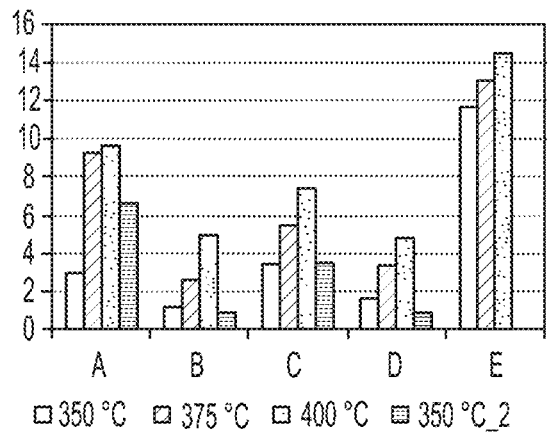
FIG. 22 is a graph of light hydrocarbon yield from an industrial heavy reformate stream obtained with commercially available zeolite catalysts, MOR-L impregnated with 0.3 wt. % rhenium, and a composite zeolite catalyst in accordance with one or more embodiments of the present disclosure.
Figure 23:
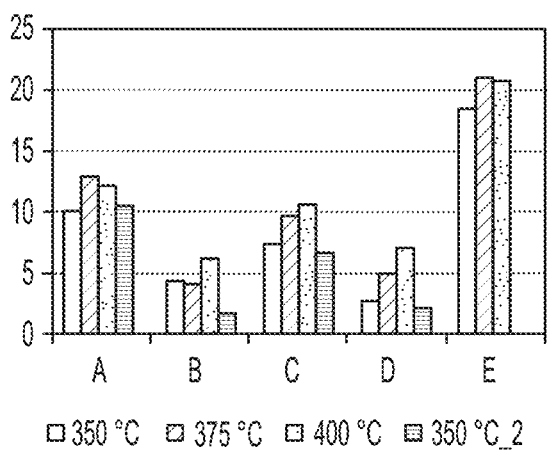
FIG. 23 is a graph of toluene yield from of an industrial heavy reformate stream obtained with commercially available zeolite catalysts, MOR-L impregnated with 0.3 wt. % rhenium, and a composite zeolite catalyst in accordance with one or more embodiments of the present disclosure.
Figure 24:
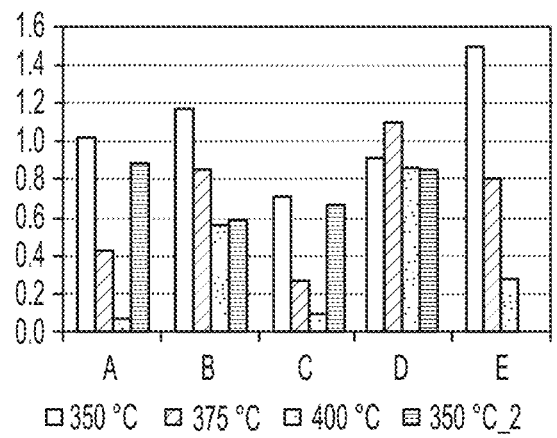
FIG. 24 is a graph of ethylbenzene yield from an industrial heavy reformate stream obtained with commercially available zeolite catalysts, MOR-L impregnated with 0.3 wt. % rhenium, and a composite zeolite catalyst in accordance with one or more embodiments of the present disclosure.
Figure 25:
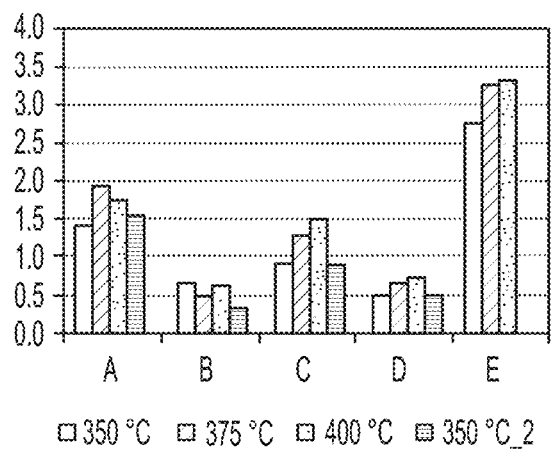
FIG. 25 is a graph of benzene yield from an industrial heavy reformate stream obtained with commercially available zeolite catalysts, MOR-L impregnated with 0.3 wt. % rhenium, and a composite zeolite catalyst in accordance with one or more embodiments of the present disclosure.

With reference to FIGS. 19, 20, 21, 22, 23, 24, and 25, the xylenes yield, A$_{10}$ yield, A$_{10+}$ yield light hydrocarbon yield, toluene yield, ethylbenzene yield, and benzene yield are respectively illustrated for each of Example 1, Comparative Example 3, Comparative Example 4, Comparative Example 7, and Comparative Example 9. It is noted, with reference to FIG. 19, that Example 1 significantly favors the xylenes production as compared to Comparative Examples 3, 4, 7, and 9 for all reaction temperatures. As xylenes are the desirable product, the increased yield of xylenes with the composite zeolite catalyst comprising MOR-L and ZSM-5 is a positive result. The higher selectivity to xylenes is believed a consequence of the lower production of undesirable A$_{10+}$ aromatics. As indicated in FIG. 21, Example 1 demonstrated the lowest yield of A$_{10+}$ aromatics. Similarly, Example 1 also demonstrates higher yields of other desirable products including toluene as shown in FIG. 23, benzene as shown in FIG. 24, and light hydrocarbons as show in FIG. 22. The numerical values of the yield as a wt. % for each catalyst is provided in Table 8. This improvement in xylenes and other light hydrocarbon production and concurrent reduction in A$_{10+}$ fraction illustrates the benefit of the methods of the present disclosure where MOR-L and ZSM-5 are in proximate contact in a single reactor during heavy reformate feed conversion. An additional advantage is that the conversion may be completed in a single reactor, thereby reducing production complexity.

TABLE 8

Product Yields

| Catalyst | Temperature | Xylenes Yield (wt. %) | $A_{10}$ Yield (wt. %) | $A_{10+}$ Yield (wt. %) | Light HC Yield (wt. %) | Toluene Yield (wt. %) | Ethylbenzene Yield (wt. %) | Benzene Yield (wt. %) |
|---|---|---|---|---|---|---|---|---|
| Example 1 | 350° C. | 20.53 | 2.85 | 4.19 | 11.72 | 2.77 | 1.49 | 18.67 |
| (60:40 weight | 375° C. | 26.00 | 1.75 | 3.57 | 13.12 | 3.28 | 0.80 | 21.06 |
| ratio | 400° C. | 29.68 | 0.97 | 3.62 | 14.56 | 3.35 | 0.28 | 20.86 |
| MOR-L:ZSM-5 with 0.3 wt. % rhenium) | | | | | | | | |
| Comp. Example 4 | 350° C. | 15.60 | 3.94 | 11.91 | 2.95 | 1.43 | 1.02 | 10.22 |
| (ATA-21) | 375° C. | 23.28 | 1.55 | 9.73 | 9.35 | 1.93 | 0.43 | 13.02 |
| | 400° C. | 24.32 | 2.72 | 12.56 | 9.62 | 1.77 | 0.06 | 12.34 |
| | 350° C. (Return) | 15.08 | 3.35 | 11.94 | 6.61 | 1.55 | 0.88 | 10.63 |
| Comp. Example 3 | 350° C. | 9.42 | 6.17 | 30.69 | 1.62 | 0.51 | 0.91 | 2.80 |
| (MOR-L with 0.3 wt. | 375° C. | 15.50 | 5.83 | 23.78 | 3.37 | 0.65 | 1.10 | 4.95 |
| % rhenium) | 400° C. | 22.46 | 4.11 | 20.95 | 4.78 | 0.75 | 0.86 | 7.13 |
| | 350° C. (Return) | 8.15 | 8.02 | 15.87 | 0.86 | 0.49 | 0.85 | 2.13 |
| Comp. Example 7 | 350° C. | 12.69 | 8.01 | 15.17 | 1.26 | 0.65 | 1.17 | 4.27 |
| (MOR with 0.3 wt. | 375° C. | 14.02 | 7.38 | 23.22 | 2.68 | 0.48 | 0.85 | 4.13 |
| % rhenium) | 400° C. | 20.71 | 5.29 | 23.87 | 4.93 | 0.63 | 0.57 | 6.31 |
| | 350° C. (Return) | 6.74 | 8.92 | 18.81 | 0.85 | 0.34 | 0.59 | 1.72 |
| Comp. Example 9 | 350° C. | 11.76 | 3.36 | 22.43 | 3.43 | 7.43 | 0.72 | 0.94 |
| (60:40 weight | 375° C. | 17.77 | 6.91 | 20.97 | 5.53 | 9.74 | 0.27 | 1.28 |
| ratio | 400° C. | 24.87 | 1.59 | 19.02 | 7.46 | 10.76 | 0.09 | 1.50 |
| MOR:ZSM-5 with 0.3 wt. % rhenium) | 350° C. (Return) | 9.53 | 5.54 | 24.84 | 3.57 | 6.77 | 0.66 | 0.91 |

It should be understood that the various aspects of the method of making BTX compounds including benzene, toluene, and xylene, and the composite zeolite catalyst utilized in the same are described and such aspects may be utilized in conjunction with various other aspects.

In a first aspect, the disclosure provides a method of making BTX compounds including benzene, toluene, and xylene. The method includes feeding heavy reformate to a reactor, the reactor containing a composite zeolite catalyst comprising a mixture of layered mordenite (MOR-L). The MOR-L comprises a layered or rod-type morphology with a layer thickness less than 30 nm and ZSM-5, where the MOR-L, the ZSM-5, or both comprise one or more impregnated metals. The method further includes producing the BTX compounds by simultaneously performing transalkylation and dealkylation of the heavy reformate in the reactor, where the composite zeolite catalyst is able to simultaneously catalyze both the transalkylation and dealkylation reactions.

In a second aspect, the disclosure provides the method of the first aspect, in which the heavy reformate comprises at least 15 wt. % methylethylbenzene (MEB) and at least 50 wt. % trimethylbenzene (TMB).

In a third aspect, the disclosure provides the method of the first or second aspects, in which the MOR-L comprises an external surface area greater than 100 m²/g.

In a fourth aspect, the disclosure provides the method of any of the first through third aspects, in which the one or more impregnated metals are selected from the group consisting of molybdenum, chromium, platinum, nickel, tungsten, palladium, ruthenium, gold, rhenium, rhodium, or combinations thereof and their respective oxides.

In a fifth aspect, the disclosure provides the method of any of the first through third aspects, in which the one or more impregnated metals comprises rhenium.

In a sixth aspect, the disclosure provides the method of any of the first through fifth aspects, in which the MOR-L, the ZSM-5, or both the MOR-L and ZSM-5 comprise up to 20 wt. % of the one or more impregnated metals.

In a seventh aspect, the disclosure provides the method of any of the first through sixth aspects, in which the composite zeolite catalyst comprises a mixture of MOR-L and ZSM-5 in a 50:50 to 90:10 weight ratio.

In an eighth aspect, the disclosure provides the method of any of the first through sixth aspects, in which the composite zeolite catalyst comprises a mixture of MOR-L and ZSM-5 in a 55:45 to 65:35 weight ratio.

In a ninth aspect, the disclosure provides the method of any of the first through eighth aspects, in which the MOR-L is impregnated with 0.25 to 0.5 wt. % rhenium.

In a tenth aspect, the disclosure provides the method of any of the first through eighth aspects, in which the ZSM-5 is impregnated with 0.25 to 0.5 wt. % rhenium.

In an eleventh aspect, the disclosure provides the method of any of the first through tenth aspects, in which the MOR-L has a molar ratio of silicon to aluminum (Si/Al) from 4:1 to 8:1.

In a twelfth aspect, the disclosure provides a composite zeolite catalyst. The composite zeolite catalyst comprises a mixture of layered mordenite (MOR-L) comprising a layered or rod-type morphology with a layer thickness less than 30 nm and ZSM-5, where the MOR-L, the ZSM-5, or both comprise one or more impregnated metals.

In a thirteenth aspect, the disclosure provides the composite zeolite catalyst of the twelfth aspect, in which the MOR-L comprises an external surface area greater than 100 m²/g.

In a fourteenth aspect, the disclosure provides the composite zeolite catalyst of the twelfth or thirteenth aspects, in which the one or more impregnated metals are selected from the group consisting of molybdenum, chromium, platinum, nickel, tungsten, palladium, ruthenium, gold, rhenium, rhodium, or combinations thereof and their respective oxides.

In a fifteenth aspect, the disclosure provides the composite zeolite catalyst of the twelfth through fourteenth aspects, in which the one or more impregnated metals comprises rhenium.

In a sixteenth aspect, the disclosure provides the composite zeolite catalyst of the twelfth through fifteenth aspects, in which the MOR-L, the ZSM-5, or both the MOR-L and ZSM-5 comprise up to 20 wt. % of the one or more impregnated metals.

In a seventeenth aspect, the disclosure provides the composite zeolite catalyst of the twelfth through sixteenth aspects, in which the composite zeolite catalyst comprises a mixture of MOR-L and ZSM-5 in a 50:50 to 90:10 weight ratio.

In an eighteenth aspect, the disclosure provides the composite zeolite catalyst of the twelfth through sixteenth aspects, in which the composite zeolite catalyst comprises a mixture of MOR-L and ZSM-5 in a 55:45 to 65:35 weight ratio.

In a nineteenth aspect, the disclosure provides the composite zeolite catalyst of the twelfth through eighteenth aspects, in which the MOR-L is impregnated with 0.25 to 0.5 wt. % rhenium.

In a twentieth aspect, the disclosure provides the composite zeolite catalyst of the twelfth through eighteenth aspects, in which the ZSM-5 is impregnated with 0.25 to 0.35 wt. % rhenium.

In a twenty-first aspect, the disclosure provides the composite zeolite catalyst of the twelfth through twentieth aspects, in which the MOR-L has a molar ratio of silicon to aluminum (Si/Al) from 4:1 to 10:1.

It should be apparent to those skilled in the art that various modifications and variations can be made to the described embodiments without departing from the spirit and scope of the claimed subject matter. Thus, it is intended that the specification cover the modifications and variations of the various described embodiments provided such modification and variations come within the scope of the appended claims and their equivalents.

Throughout this disclosure ranges are provided. It is envisioned that each discrete value encompassed by the ranges are also included. Additionally, the ranges which may be formed by each discrete value encompassed by the explicitly disclosed ranges are equally envisioned.

What is claimed is:

1. A method of making BTX compounds including benzene, toluene, and xylene, the method comprising:
   feeding heavy reformate to a reactor, the reactor containing a composite zeolite catalyst comprising a mixture of layered mordenite (MOR-L) comprising a rod morphology with a smallest dimension less than 28 nm and ZSM-5, where the MOR-L or both the MOR-L and ZSM-5 comprise one or more impregnated metals and the MOR-L without the impregnated metals comprises an external surface area greater than 120 $m^2/g$; and
   producing the BTX compounds by simultaneously performing transalkylation and dealkylation of the heavy reformate in the reactor, where the composite zeolite catalyst is able to simultaneously catalyze both the transalkylation and dealkylation reactions,
   wherein the MOR-L has a molar ratio of silicon to aluminum (Si/Al) from 4:1 to 8:1.

2. The method of claim 1, where the heavy reformate comprises at least 15 wt. % methylethylbenzene (MEB) and at least 50 wt. % trimethylbenzene (TMB).

3. The method of claim 1, where the one or more impregnated metals are selected from the group consisting of molybdenum, chromium, platinum, nickel, tungsten, palladium, ruthenium, gold, rhenium, rhodium, or combinations thereof and their respective oxides.

4. The method of claim 1, where the one or more impregnated metals comprises rhenium.

5. The method of claim 1, where the MOR-L, the ZSM-5, or both the MOR-L and ZSM-5 comprise up to 20 wt. % of the one or more impregnated metals.

6. The method of claim 1, where the composite zeolite catalyst comprises a mixture of MOR-L and ZSM-5 in a 50:50 to 90:10 weight ratio.

7. The method of claim 1, where the MOR-L is impregnated with 0.25 to 0.5 wt. % rhenium.

8. The method of claim 1, where the ZSM-5 is impregnated with 0.25 to 0.5 wt. % rhenium.

* * * * *